(12) United States Patent
Meeks

(10) Patent No.: US 7,345,751 B2
(45) Date of Patent: Mar. 18, 2008

(54) MATERIAL INDEPENDENT OPTICAL PROFILOMETER

(75) Inventor: Steven W. Meeks, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 204 days.

(21) Appl. No.: 11/268,215

(22) Filed: Nov. 7, 2005

(65) Prior Publication Data

US 2006/0072126 A1  Apr. 6, 2006

Related U.S. Application Data

(63) Continuation of application No. 10/444,652, filed on May 22, 2003, now Pat. No. 7,123,357, which is a continuation-in-part of application No. 10/219,632, filed on Aug. 14, 2002, now Pat. No. 6,909,500, which is a continuation-in-part of application No. 10/126,154, filed on Apr. 19, 2002, now Pat. No. 6,930,765, which is a continuation-in-part of application No. 10/029,957, filed on Dec. 21, 2001, now Pat. No. 6,897,957, which is a continuation-in-part of application No. 09/861,280, filed on May 18, 2001, now Pat. No. 6,757,056, which is a continuation of application No. 09/818,199, filed on Mar. 26, 2001, now abandoned.

(51) Int. Cl.
  *G01N 21/00* (2006.01)
(52) U.S. Cl. ................. 356/237.2; 356/237.4
(58) Field of Classification Search ............ None
  See application file for complete search history.

(56) References Cited

U.S. PATENT DOCUMENTS

| 3,734,626 A | * | 5/1973 | Roberts et al. ............ 356/613 |
| 4,310,242 A | * | 1/1982 | Genco et al. ............. 356/128 |
| 4,863,268 A | * | 9/1989 | Clarke et al. ............ 356/237.2 |

* cited by examiner

*Primary Examiner*—Michael P. Stafira
(74) *Attorney, Agent, or Firm*—Caven & Aghevli LLC

(57) ABSTRACT

A system and method for measuring defects, film thickness, contamination, particles and height of a thin film disk or a silicon wafer. The system includes a processor for determining height. In addition to measuring the height the system can measure film thickness and defects through the measurement of the phase shift of optical signals. An optical profilometer is described which can measure topography on thin film disks, optical substrates or silicon wafers and whose output is independent of the reflectivity of the substrate. This material independent optical profilometer uses a retro-reflector to achieve reflectivity independence and to increase the height sensitivity to 8 times the height of the surface. The reflectivity independent optical profilometer achieves perfect cancellation of the slope of the surface while measuring the topography of the substrate.

25 Claims, 30 Drawing Sheets

MATERIAL INDEPENDENT OPTICAL PROFILOMETER

RELATED APPLICATIONS

This application is a continuation of commonly assigned U.S. patent application Ser. No. 10/444,652, entitled Method of Detecting and Classifying Scratches and Particles on Thin Film Disks or Wafers, by Steven W. Meeks, filed May 22, 2003 now U.S. Pat. No. 7,123,357, which is a continuation-in-part of U.S. patent application Ser. No. 10/219,632 filed on Aug. 14, 2002, (U.S. Pat. No. 6,909,500) which is a continuation-in-part of U.S. patent application Ser. No. 10/126,154 filed on Apr. 19, 2002, (U.S. Pat. No. 6,930,765) which is a continuation-in-part of U.S. patent application Ser. No. 10/029,957 filed on Dec. 21, 2001, (U.S. Pat. No. 6,897,957) which is a continuation-in-part of U.S. patent application Ser. No. 09/861,280 (U.S. Pat. No. 6,757,056) filed on May 18, 2001, which is a continuation of U.S. patent application Ser. No. 09/818,199 filed on Mar. 26, 2001 now abandoned, which are all incorporated by reference herein in their entirety.

This application is also related to U.S. patent application Ser. No. 09/718,054 filed on Nov. 20, 2000, which is a continuation-in-part of U.S. patent application Ser. No. 09/414,388 filed on Oct. 7, 1999, which is a continuation-in-part of U.S. patent application Ser. No. 09/347,622 filed on Jul. 2, 1999, which is a continuation-in-part of U.S. Pat. No. 6,031,615, which claims priority from provisional application No. 60/059,740 filed on Sep. 2, 1997, which are all incorporated by reference herein in their entirety.

BACKGROUND

1. Field of the Invention

The present invention is directed toward measuring thin films and defects on silicon wafers, magnetic thin film disks and transparent and coated glass substrates and more particularly toward measuring thin film thickness, and wear, surface roughness, scratches, particles, stains, pits, mounds, surface topography, step heights, and inclusions using a laser directed toward a thin film disk at many angles including non-Brewster's angles of an absorbing layer of the thin film.

2. Description of Background Art

Coated thin film disks are used in a variety of industries including the semiconductor and the magnetic hard disk industry. A computer hard disk (magnetic storage device) is a non-volatile memory device that can store large amounts of data. One problem that the manufacturers of hard disks experience is how to maximize the operating life of a hard disk. When a hard disk fails the data stored therein may be difficult, expensive, or impossible to retrieve. Failure of a hard disk may be caused by defects on the surface of the thin film disk. It-is important to be able to detect and classify these defects in order to prevent disk drive failure and to control the manufacturing process.

A schematic of a thin film disk used in magnetic storage devices is shown in FIG. 1. It includes a magnetic thin film (layer) 106 which is deposited upon a substrate 108 (typically a NiP plated Al—Mg alloy or glass). The magnetic thin film 106 can be protected by a thin film of carbon 104 (carbon layer), for example, whose thickness is typically 20 to 200 Angstroms (.ANG.). The carbon layer 104 is typically coated with a thin layer (10 to 30 Angstroms) of a fluorocarbon lubricant 102 (lubricant layer). The lubricant layer 102 serves to increase the durability of the underlying carbon layer 104 particularly when the magnetic read/write head contacts the disk, for example when the disk drive is turned off. The hard disk drive industry has been dramatically improving storage capacity by flying the thin film head closer to the surface of the thin film disk. As a result even very small defects can cause a hard drive to fail. These defects may be topographic such as scratches, pits, mounds, or particles or they may be non-topographic such as stains or inclusions. It is useful to measure all these types of defects to control the disk manufacturing process and improve disk drive manufacturing yield.

A schematic of a semiconductor wafer is shown in FIG. 2. The structure of a semiconductor wafer can be very complex and FIG. 2 shows only a typical structure of a wafer that is undergoing the copper dual damascene process. In FIG. 2, 201 is the copper layer 202 is the second plasma enhanced chemical vapor deposited (PECVD) oxide layer, 203 is the first PECVD oxide layer and 204 is the silicon substrate. The copper layer 201 is polished down using a chemical mechanical polishing (CMP) process until only the via holes and copper lines remain. The problem is that the CMP process can leave residual copper, nitride, or CMP slurry on the surface of the wafer. In addition, stains, particles, scratches, and micro-waviness may be present on the polished wafer. It is useful to detect and measure such defects to control the process of making the wafer. Fewer defects will also mean greater wafer yields at the end of the process. The problem in the hard disk, semiconductor and photonics industries is to inspect these magnetic disks and wafers for defects such as particles, scratches, pits, mounds, stains, topographic irregularities and inclusions. Conventional techniques to solve these problems are discussed in U.S. Pat. Nos. 4,674,875, 5,694,214, 5,748,305, and 6,157,444 that are all incorporated by reference herein in their entirety. These patents describe techniques to measure defects using essentially sophisticated scatterometers and reflectometers. None of these systems enables the simultaneous measurement of topographic and non-topographic defects. The present invention enables this measurement through the use of a combined reflectometer, scatterometer, ellipsometer, profilometer and Kerr effect microscope.

What is needed is a system and method for examining thin film disks, silicon wafers and transparent wafers that: (1) measures topographic and non-topographic defects; (2) measures the optical profile on these substrates; (3) enables the measurements to be performed simultaneously; (4) measures the thickness of thin films; (5) enables measurement on patterned or unpatterned silicon or photonic wafers; (6) is performed in situ or in line; (7) measures only a single side of a transparent substrate or (8) is configurable to have multiple selectable beam widths to test varying spot sizes of the object being examined.

As the technology for the semiconductor and the disk drive industries continues to advance there is a need to detect and classify ever smaller defects. When a defect is smaller in size than the dimension of a measurement beam, it is difficult to determine the nature of the defect. What is needed is a method for identifying and classifying defects regardless of the relative size of the measurement beam.

SUMMARY

A system and method for measuring topographic and non-topographic defects and topography on thin film magnetic disks, silicon wafers and transparent substrates. This invention enables the measurement of the height of a defect on a thin film disk or a silicon wafer having a first electromagnetic signal source for generating a first signal toward a first position on the thin film magnetic disk at a first angle, a second electromagnetic signal source for generating a second signal toward the first position on the thin film magnetic disk at a second angle, a spinning device for rotating the object to change the first position, a first position sensitive detector to receive a portion of the first signal that reflects off of the object, and to determine a radial portion of the first signal (S1$r$) and a circumferential portion of the first signal (S1$c$), a second position sensitive detector positioned at a right angle from the first position sensitive detector, to receive a reflected portion of the second signal that reflects off of the object, and to determine a radial portion of the second signal (S2$r$) and a circumferential portion of the second signal (S2$c$). The system also includes a processor for determining the height of the first position based upon a difference between S2$c$ and S1$c$ that does not include slope information. The system also enables the detection of topographic and non-topographic defects through the measurement of the phase shift of the optical wave. A special feature of this invention is its ability to remove a semiconductor pattern from the data and enhance the presence of defects on the patterned silicon or photonics wafer. Several miniaturized embodiments are presented that enable measurement on both sides of disks or wafers. A focused beam optical profilometer is described which separates slope and height and is independent of the reflectivity of the material.

DETAILED DESCRIPTION

A preferred embodiment of the present invention is now described with reference to the figures where like reference numbers indicate identical or functionally similar elements. Also in the figures, the left most digit(s) of each reference number correspond(s) to the figure in which the reference number is first used.

Figure 1:
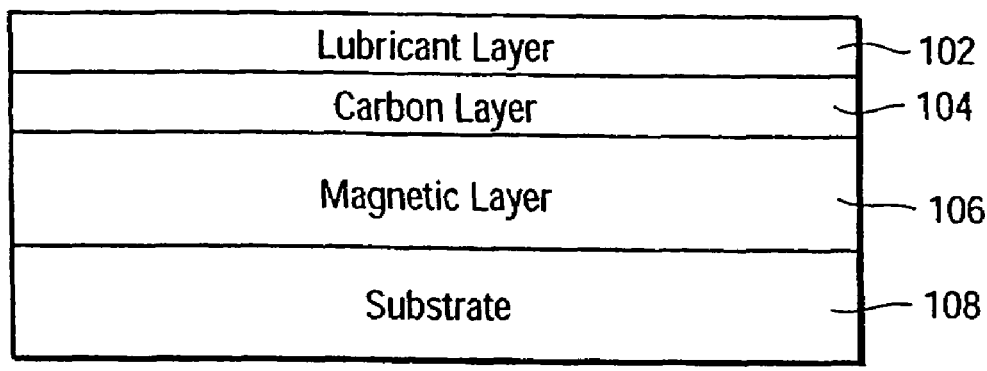
FIG. 1 is an illustration of a thin film that can be measured using an embodiment of the present invention.
Figure 2:
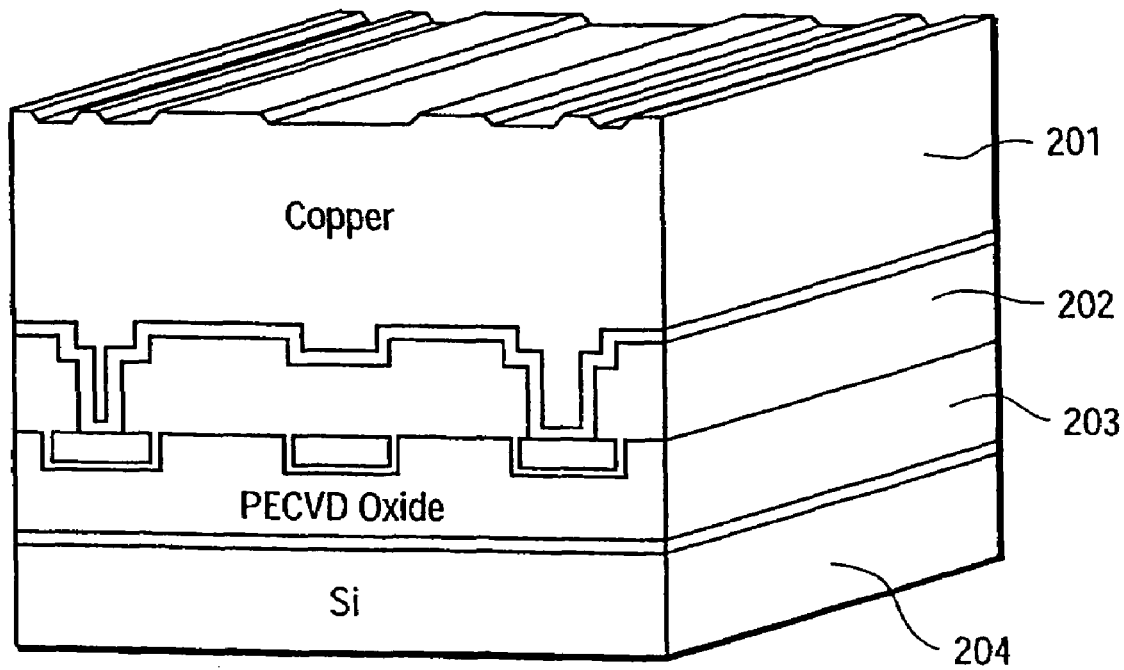
FIG. 2 is an illustration of a semiconductor wafer that can be measured with one embodiment of the present invention.
Figure 3:
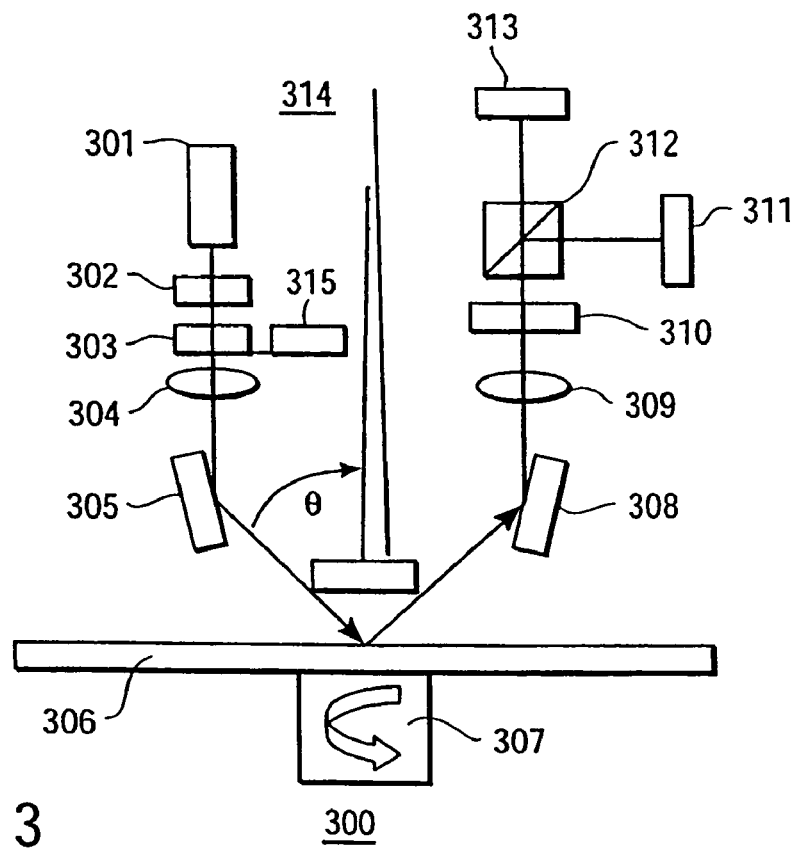
FIG. 3 is one half of optical layout of combined ellipsometer and optical profiler (side view).

FIG. 3 is an illustration of an apparatus for measuring properties of the thin film according to an embodiment of the present invention. The apparatus uses a focused laser light signal whose angle of propagation $\theta$ (as shown in FIG. 3) can be between zero degrees from normal and ninety degrees from normal.

One embodiment of the apparatus 300 includes a conventional laser diode 301, e.g., RLD65MZT1 or RLD-78MD available from Rolm Corporation, Kyoto, Japan, which has been collimated by Hoetron Corp., Sunnyvale, Calif., e.g., a conventional linear polarizer 302, e.g., made of Polarcor that is commercially available from Newport Corp., Irvine, Calif., a conventional zero order half wave plate 303 that is commercially available from CVI Laser, Livermore Calif., a conventional focusing lens 304 that is commercially available from Newport Corporation, Irvine, Calif., conventional mirrors 305 and 306 available from Newport Corp. Irving, Calif. A collimating lens 309 available from Newport Corp., a zero order quarter wave plate 310 available from CVI Laser Corp., a conventional polarizing beam splitter 312 rotated at 45° to the plane of incidence available from CVI Laser Corp., a pair of conventional quadrant detectors 311 and 313 available from Hamamatsu Corp., Hamamatsu City, Japan, a conventional avalanche photodiode 314 available from Advanced Photonix, Inc., Camarillo, Calif. and a conventional motor 315 available from Maxon Precision Motors, Burlingame, Calif. for rotating the half wave plate 303. The avalanche photodiode 314 may be replaced with a conventional photo multiplier tube (PMT) available from Hamamatsu Corp., Hamamatsu City, Japan.

It will be apparent to persons skilled in the art that the apparatus 300 is an embodiment of the present invention and that alternate designs can be used without departing from the present invention. The operation of the apparatus 300 is now described in greater detail.

A laser diode 301 emits an electromagnetic signal toward the thin film disk, silicon wafer, photonics wafer or glass substrate. In an embodiment the electromagnetic signal is a light signal having a wavelength of 780 or 655 nanometers (nm) although a wide variety of wavelengths can be used. The angle of propagation of the light signal can be any angle $\theta$ between zero and ninety degrees.

Laser diodes are well known to have an internal photodiode to monitor the laser output power. An embodiment of a feedback control circuit to control the optical intensity is to use such a photodiode, which is internal to the laser diode. This photodiode which is internal to the laser diode feeds back a control signal to negative feedback circuitry and by doing so keeps the intensity of the laser at a constant value. The photodiode that is used to control the laser intensity may be external to the laser. When an external photodiode is used an external non-polarizing beam splitter is placed after the laser. This external non-polarizing beam splitter directs a sample of the laser onto the external photodiode. The signal from the external photodiode is used to feedback a control signal to negative feedback circuitry and thereby controls the laser intensity. Another means of keeping an approximate constant output power of the laser is to control the current of the laser diode, that is, run the diode laser in a constant current mode. The laser diode will exhibit a very slow decrease in output power over a period of months. As long as the scan time is less than 5 or 10 minutes then the optical power output of the laser will remain constant during the scan. The advantage of this technique is its simplicity. Long-term drifts of the laser output power may be calibrated out of the system by first measuring a standard reflector and using this to normalize the measured signals. The value of the signal is first measured over the standard (known) reflector and then the disk or wafer is measured. If there has been any drift of the standard reflector measurement then all the data is corrected for this amount of drift. As a result long-term drifts may be compensated even when operating in a constant current mode. The emitted light passes through the linear polarizer 302. The linear polarizer 302 improves the linear polarization of the laser light signal.

There are several ways to reduce the optical noise of lasers. One of these is to use a multi-mode laser diode (such as the Rohm laser diode mentioned above) that runs in 6 to 8 longitudinal modes simultaneously. This prevents the laser from mode hopping and reduces intensity noise. Another way to reduce noise is to start with a single mode laser and to modulate the laser current at a frequency from 30 to 1000 MHz. The laser current includes a DC component of 20 to 100 ma plus a smaller AC component at the above specified frequency. The AC component of the current forces the single mode laser to run in several modes and this prevents mode hopping and reduces laser noise. This technology is known as noise reduction through mode modulation. A third way to reduce noise is to use a thermoelectric cooler (TEC) to keep the laser temperature constant. The TEC technology will reduce mode hopping but will not prevent it. The TEC technology will also increase the diode laser lifetime.

Figure 35:
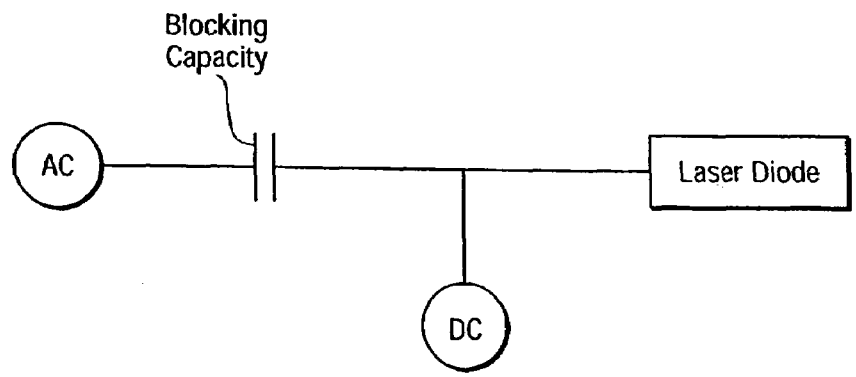
FIG. 35 is an illustration of mode modulation circuitry according to one embodiment of the present invention.

The mode modulation technology is useful in instruments like the Optical Surface Analyzer discussed herein. This is because the laser noise and intensity stability limits the sensitivity of the instrument. The best way to eliminate mode hopping is to use mode modulation. FIG. 35 shows a schematic of the mode modulation technology. The 30 to 1000 MHz modulation comes from the AC source and the DC source provides the 20 to 100 ma DC current needed to run the laser. The blocking capacitor prevents the DC current from passing into the AC source. When this technology is combined with the Optical Surface Analyzer described herein the sensitivity of the instrument can be greatly improved. Further improvements may be achieved by combining TEC with mode modulation technology.

The linearly polarized light passes through a mechanically rotatable zero order half-wave plate 303. The half wave plate 303 is attached to a miniature motor 315 which allows the polarization to be dynamically rotated between P polarized (parallel to the plane of incidence), S polarized (perpendicular to the plane of incidence) and 45° polarized (between P and S) light. The polarized light passes through a focusing lens 304 and is directed onto a thin film magnetic disk, silicon wafer or transparent substrate 306 by a turning mirror 305. The reflected signal is directed to the detection optics by another turning mirror 308 and recollimated by another lens 309. An avalanche photodiode, conventional PIN photodiode or photo multiplier tube 314, for example, detects the scattered component of the signal. The recollimated beam passes through a zero order quarter wave plate 310 that is used to adjust the polarization of the beam so that equal amounts of energy are directed into the quadrant photodetectors 313 and 311. After passing through the quarter wave plate 310 the beam is split by a polarization beam splitter 312 that is rotated by 45° to the plane of incidence. In another embodiment the polarizing beam splitter may be a Wollaston prism or a Glan Thompson or a Rochon prism beam splitter. The split beams are directed onto two quadrant detectors 311 and 313. The quadrant detectors are used to compute the phase shift between the split beams, the reflectivity, the optical profiles in the radial and circumferential directions, and the Kerr rotation (if the film on the substrate 306 is magnetic). The outputs from the quadrant detectors are digitized by a conventional analog to digital converter and directed to the memory of a conventional personal computer. The signals are then analyzed by the personal computer to detect defects, measure topography, and measure stains. The entire optical apparatus 300 is placed upon a stage that moves the apparatus in the radial direction while a motor 307 rotates the sample 306. In this manner the entire surface of the sample 306 may be scanned for defects.

An alternative embodiment for scanning the entire substrate 306 is to place the optical head or the substrate 306 on a x-y scan stage. The substrate 306 or the optical apparatus 300 is scanned in the x and y directions and in this manner the entire sample may be scanned for defects or topography.

The spindle or motor which rotates the disk at a high rate of speed includes an encoder which produces 1024 pulses as it rotates through 360 degrees, for example. This encoder is used to determine the circumferential positions around the disk. The present invention preferably utilizes a very high-resolution determination of the position around the circumference of the disk. This is accomplished by using a phase locked loop to multiply the encoder signal by a selectable factor of up to 64 times. The phase locked loop, which multiplies the 1024 encoder pulses, has the ability to track any velocity jitter in the encoder. This feature allows averaging of repeated revolutions to be done with no loss of lateral resolution. That is, subsequent revolutions lie in phase with one another and when averaged, the resulting image is not smeared by any jitter effect. Averaging is done to improve signal-to-noise ratio.

Figure 4:
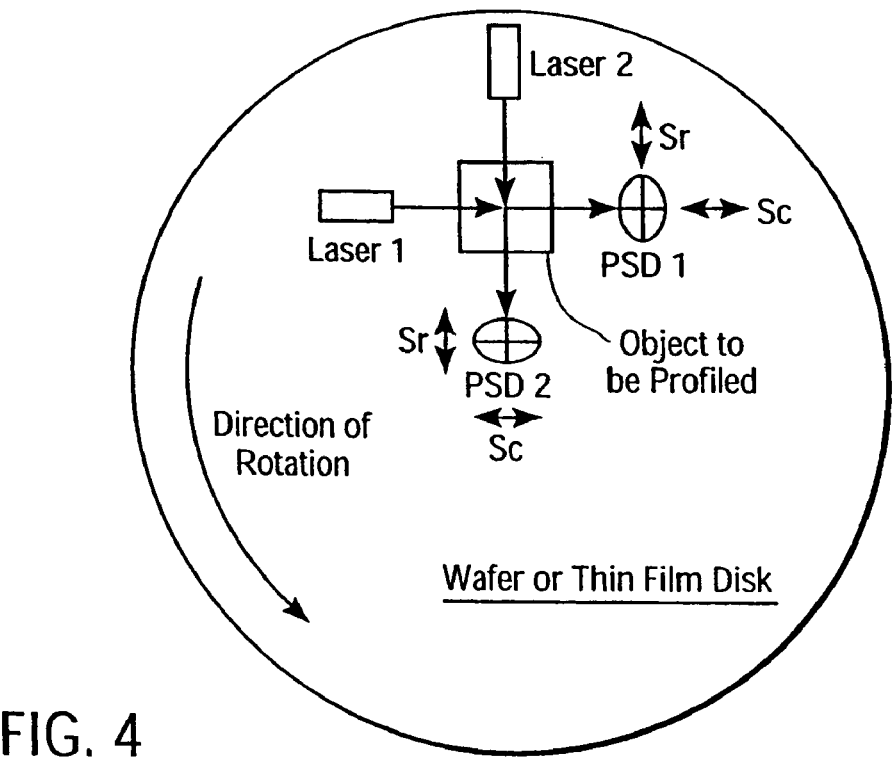
FIG. 4 is a top view of an optical profilometer that measures height or slope according to one embodiment of the present invention.

FIG. 4 shows the top view design of an optical profilometer, which measures height only and measures height directly. It can also measure the slope of the surface independent of height. This differs from previous optical profilometers that measure both slope and height at the same time. With such systems the height is obtained from the slope data by integrating the slope information. However, if the slope information is contaminated with height information then the integration will not give the correct surface profile. A goal is to obtain data that includes only height information and not a combination of both slope and height. The design illustrated and described with reference to FIGS. 4-7 accomplishes this by using two lasers and two position sensitive detectors (PSD) oriented at right angles to one another.

The position sensitive detectors (PSD) are quadrant detectors that are oriented as shown in FIG. 4. The PSD's measure the displacement of the beam in the radial and circumferential directions by subtracting the appropriate PSD quadrants. As the laser beam moves along the surface of the object to be measured, the roughness and waviness of the surface cause the laser beam to "wiggle" on the quadrant detector in response to the slope of the surface. The quadrant detector measures this by subtracting the sum of one pair of quadrants from the sum of another pair. For example, referring to FIG. 6, the slope of the surface in the circumferential direction is given by $[(A1+B1)-(C1+D1)]/[A1+B1+C1+D1]$ where the sum of the four quadrants in the denominator is used to normalize for reflectivity differences. At the same time, if the average distance of the surface from the detector changes, then the average position of the beam on the quadrant detector will change. The resulting difference signal in the above equation will register a slope change when in fact a difference in surface height is occurring. The problem is to be able to separate slope changes from height changes. This can be accomplished by considering the slope in the radial direction, which is obtained by referring to FIG. 6 and is given by $[(A1+D1)-(B1+C1)]/[A1+B1+C1+D1]$. The equation for the radial slope measures the "wiggle" of the beam in the radial direction. In the case of the radial slope, if the average distance of the surface from the detector changes then the beam simply moves along the line separating A1+D1 from B1+C1. As a result the radial slope signal does not change when the surface height changes and the equation for the radial slope records only slope and not height changes.

When the orientation of the laser beam is rotated by 90 degrees (as with laser 2 and PSD 2 in FIG. 4) the behavior of the radial and circumferential slope will reverse. In the case of laser 2 and PSD 2 the circumferential slope equation will record only slope changes and not height changes. On the other hand, for laser 2, the radial slope equation will record both slope and height changes. Since the output beam of both lasers 1 and 2 is positioned at the same location on the surface (as shown in FIG. 4) then it is possible to subtract the radial slope equation from laser 1 and PSD 1 from the radial slope equation from laser 2 and PSD 2. The resulting subtraction will include only height information and no slope information. It is also possible to obtain the same information by subtracting the circumferential slope equation from laser 1 and PSD 1 from the circumferential slope equation from laser 2 and PSD 2. The radial slope (with no height information) can be obtained by choosing the radial slope equation from laser 1 and PSD 1. The circumferential slope (with no height information) can be obtained by choosing the circumferential slope equation from laser 2 and PSD 2. In this manner it is possible to independently measure surface height variation and slope variation.

Figure 5:
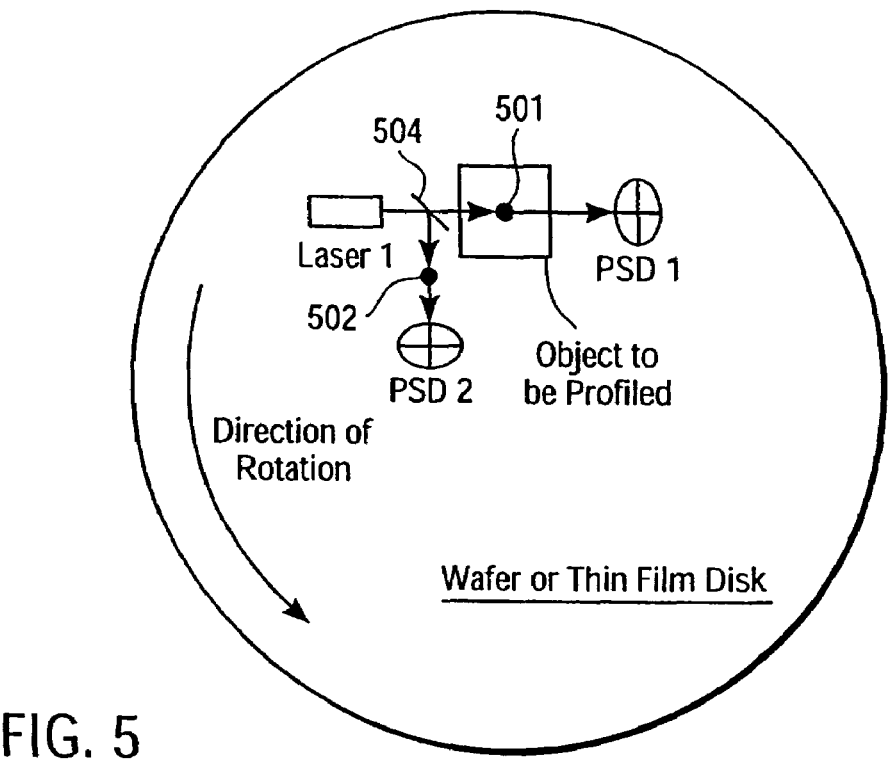
FIG. 5 is a top view of an optical profilometer having a single laser that measures height or slope according to another embodiment of the present invention.

In another embodiment of this optical profilometer, as shown in FIG. 5, a single laser is used and a 50/50 mirror 504 oriented at a compound angle directs a second beam onto the surface to a position labeled 502 on FIG. 5. The beam that passes through the 50/50 mirror 504 is directed onto the surface to a position labeled 501 on FIG. 5. The entire surface of the object to be measured is scanned with both of the beams resulting in at least two images of the surface. The resulting images are stored and digitally shifted so that the resulting images have the object to be profiled at the same x, y location. The resulting shifted images may then be subtracted to give the height profile in the manner described above. The advantage of this embodiment is that it uses only a single laser and fewer optical components and the beam shape of the two beams is identical.

Laser one and PSD 1 nominally measure the signal in the radial, Sr, and the signal in the circumferential, Sc, directions. However, the nature of the PSD results in Sc from laser one and PSD 1 being contaminated with height information, in addition to slope information. Sr from laser 1 and PSD 1 include only slope information. Laser two and PSD 2 also nominally measure the slope in the radial and circumferential directions. However, Sr from laser 2 and PSD 2 measures both slope and height at the same positions as Sr from laser 1 and PSD 1. As a result the true height variation can be obtained by subtracting Sr from laser 2 and PSD 2 from Sr from laser 1 and PSD 1. That is, the slope information is removed when subtracting Sr from PSD 2 from Sr from PSD 1, leaving only the height information.

A similar result can be obtained from subtracting Sc from PSD 2 that only includes slope information. As a result, subtracting Sc from PSD 2 from Sc from PSD 1 gives data including only height information. The result is a direct measurement of height. The advantages of this technique are that it gives a direct measurement of height and it can be done in a non-contact manner at high speed. This technique can also measure step heights with 90-degree step angles. Conventional systems, which use slope measurements, cannot measure 90-degree step heights.

Figure 6:
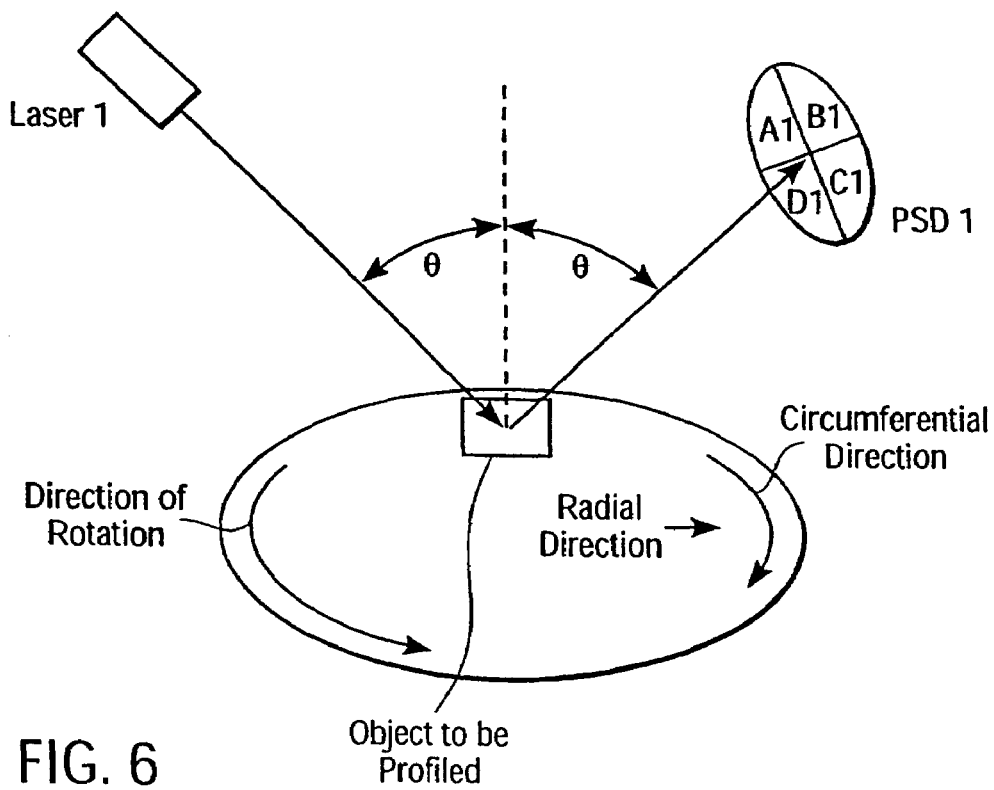
FIG. 6 is a side view of optical profilometer showing laser one and PSD 1 according to one embodiment of the present invention.

FIG. 6 shows the side view design of the optical profilometer. This figure only shows laser 1 and PSD 1 in an effort to easily show the side view design. In FIG. 6 the optical profilometer is positioned above a thin film disk or wafer and is translated in the radial direction while the disk or semiconductor wafer is rotated.

Figure 7:
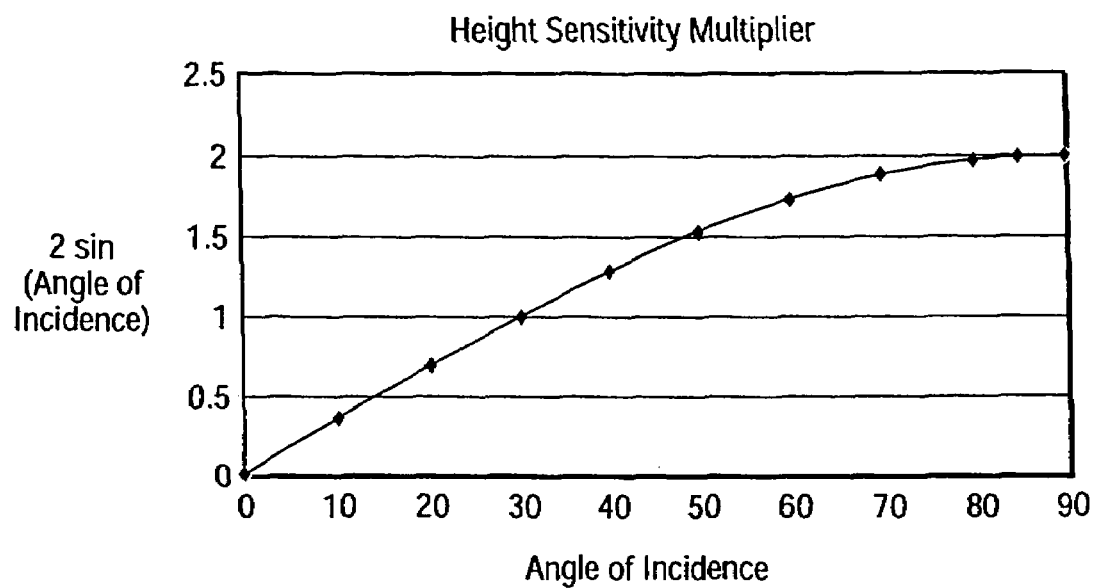
FIG. 7 illustrates the height sensitivity multiplier as a function of angle of incidence (theta) according to one embodiment of the present invention.

The angle of incidence ($\theta$) shown in FIG. 6 can be chosen for the particular application. Any angle of incidence can be chosen except normal incidence, where the PSD's would have no height sensitivity. For an application that involves transparent substrates one could choose angles greater than 45 degrees in order to increase the reflection signal from the surface. As the angle of incidence increases, the height sensitivity also increases by the factor $2 \sin \theta$. A plot of this factor is shown in FIG. 7. This suggests that an angle of incidence greater than or equal to approximately 60 degrees would be optimal, although not necessary. At angles greater than 60 degrees the sensitivity will increase and the signal from a transparent surface will increase. This embodiment requires that the focused spot sizes of the two lasers be substantially identical and that the laser spots overlap as closely as possible.

Figure 8:
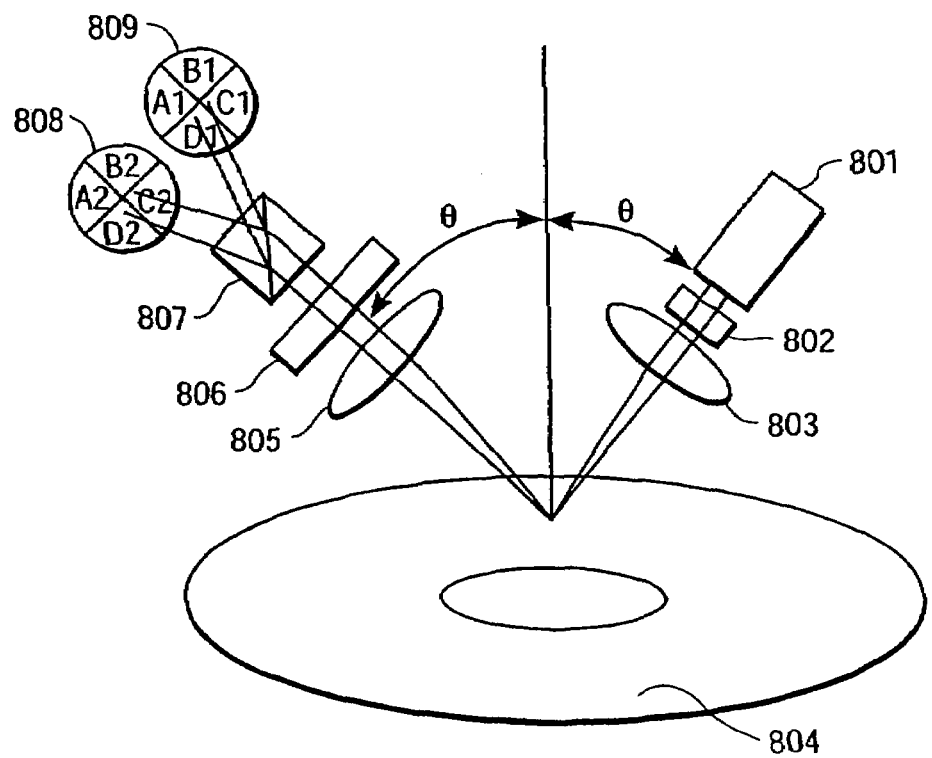
FIG. 8 is an illustration of a miniature optical surface analyzer according to one embodiment of the present invention.
Figure 9:
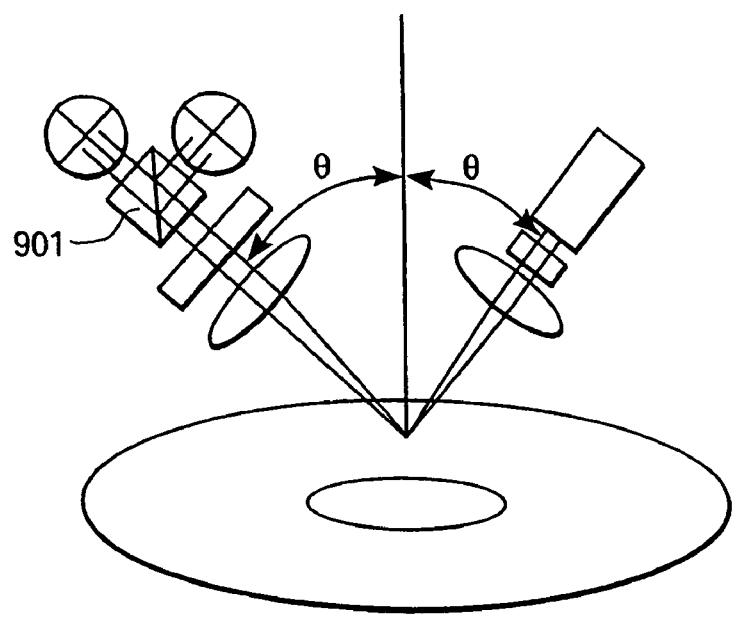
FIG. 9 is an illustration of a miniature optical surface analyzer according to another embodiment of the present invention.

A problem in the magnetic recording industry is to inspect thin film disks for defects at the final test step of the manufacturer of disks. The manufacturers of thin film disks require that both sides of the thin film disk be inspected simultaneously. The problem is that the clearance between the disk and the chuck (which holds the disk) is only 1" or less (see FIG. 13, 1304). This requires that the optics be miniaturized in order to fit in the small space between the disk and the chuck (see FIG. 13). A solution to this problem can be obtained by using the optical designs in FIGS. 8, 9, 10, and 11. These designs have several key improvements, which allow the design to be miniaturized without compromising the performance of the device. First of all the design uses the internal feedback photodiode, which is included within the laser diode 801, to achieve stabilization of the DC level of the optical signal. Secondly, the angle of incidence, $\theta$, is adjusted to reduce the height of the instrument so that it will fit within the 1" space requirement. Thirdly, the surface topography measurement capability feature of the instrument is incorporated within the phase/specular detectors 808 and 809 shown in FIGS. 8 and 9. The position sensitive detectors 808 and 809 (quadrant detectors) serve as both phase detectors, specular detectors, and topography measurement detectors. Fourthly, the size may be decreased by using a polarizing beam splitter 901 as shown in FIG. 9 instead of a Wollaston prism 807 as shown in FIG. 8. The polarizing beam splitter 807 or Wollaston prism 901 is rotated at 45° with respect to the plane of incidence.

Figure 10:
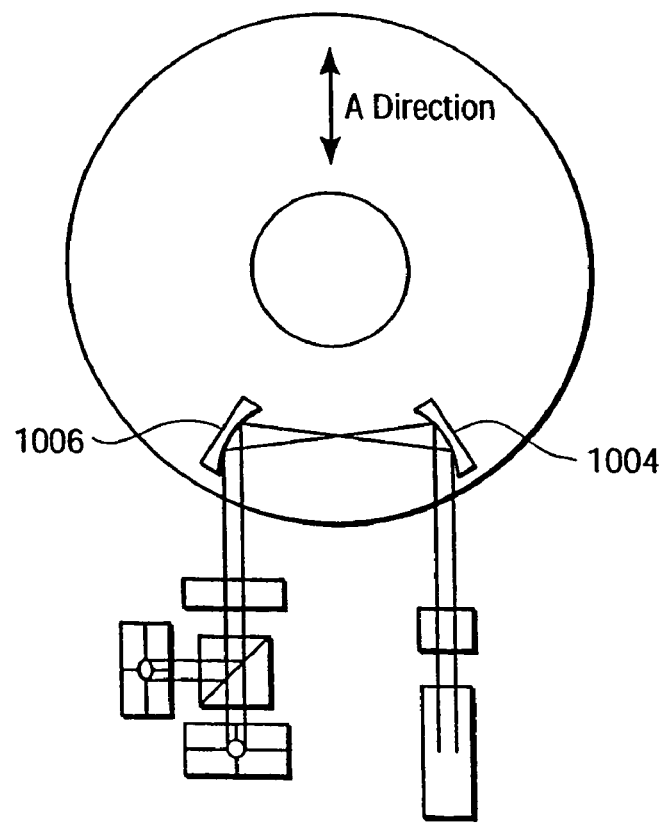
FIG. 10 is an illustration of a miniature optical surface analyzer according to another embodiment of the present invention from a top view perspective.
Figure 11:
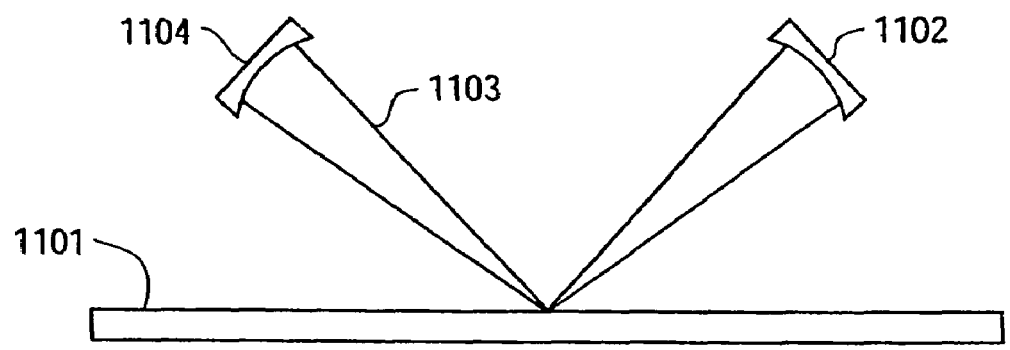
FIG. 11 is an illustration of a miniature optical surface analyzer of FIG. 10 from the perspective from the A direction.
Figure 12:
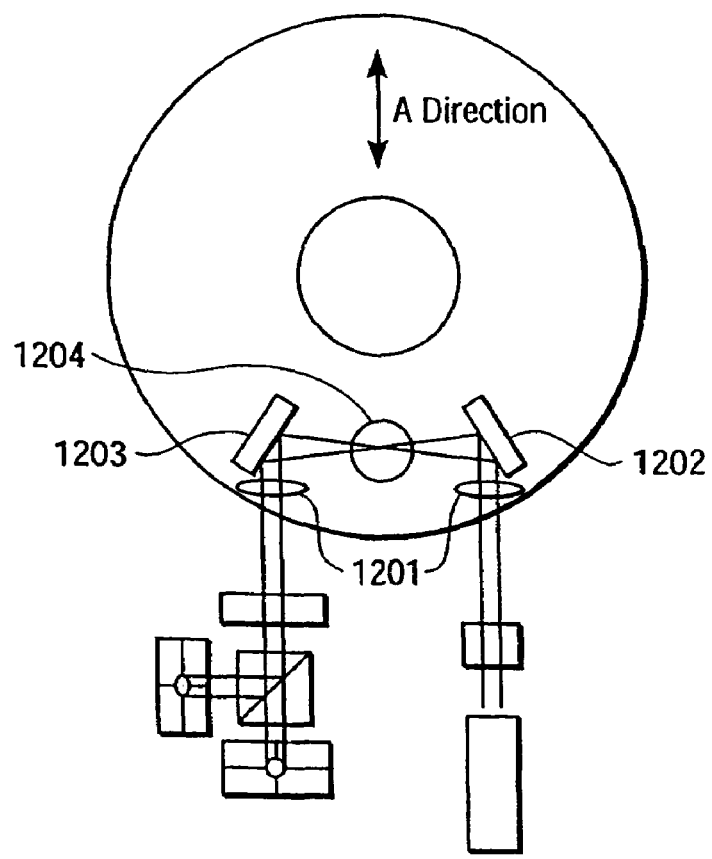
FIG. 12 is an illustration of a miniature optical surface analyzer according to another embodiment of the present invention from a top view perspective.

Another embodiment of this invention can use a beam splitter that splits the beam into non-orthogonal components, which will be discussed in a subsequent section. Using two spherical mirrors 1004 and 1006 to direct the beam onto the disk as shown in FIG. 10 will diminish the size in the lateral dimension. The mirrors 1004 and 1006 are adjusted at a compound angle as shown in FIG. 10. This is also shown in FIG. 11 which is a view of FIG. 10 along the "A" direction, where the mirrors that are at a compound angle are 1102 and 1104. These mirrors direct the beam 1103 onto the disk or wafer 1101. In addition to directing the beam onto the disk the spherical mirrors also focus the beam to a small spot. In an alternative embodiment flat mirrors 1202 and 1203 are used in combination with focusing lenses 1201 as shown in FIG. 12. Also shown in FIG. 12 is a silicon photodetector or avalanche photodiode or photo multiplier tube 1204, which is positioned above the point where the beam strikes the disk. This element enables the detection of submicron particles. The avalanche photodiode 1204 is available from Advanced Photonix, Inc., Camarillo, Calif.

Referring to FIG. 8, the laser beam from the diode laser 801 passes through a linear polarizer 802, and a focusing lens 803 and then strikes a disk or wafer 804. Upon reflecting from the surface the beam passes through a recollimating lens 805, a quarter wave plate 806, and through a polarizing beam splitter such as Wollaston prism 807 which is rotated at 45° to the plane of incidence and onto two quadrant detectors 808 and 809. The specular signal is obtained by summing the signals from position sensitive detector 1809 with the sum of position sensitive detector 2, 808 times a constant κ:

Specular Signal=(*A*1+*B*1+*C*1+*D*1)+κ(*A*2+*B*2+*C*2+*D*2)

The cosine of the phase shift between the two split beams (Cos(ps)) can be obtained by subtracting the sum of the elements of detector 1809 from those of detector 2, 808 times a constant K:

Cos(*ps*)=(*A*1+*B*1+*C*1+*D*1)=K(*A*2+*B*2+*C*2+*D*2) where K is a constant

Referring to FIG. 8 detector 1, 809, the slope in the circumferential direction is given by:

Slope in Circumferential Direction=[(*B*1+*C*1)−(*A*1+*D*1)]/(*A*1+*B*1+*C*1+*D*1)

The slope in the radial direction is given by:

Slope in Radial Direction=[(*A*1+*B*1)−(*C*1+*D*1)]/(*A*1+*B*1+*C*1+*D*1)

The topography in the circumferential or radial direction is obtained by integrating the slope in the circumferential or radial direction, respectively. The slope signals can also be obtained from detector 2, 808 with the same equations as shown above except for substituting 2 for 1.

Using the designs in FIGS. 8, 9, 10 and 12 will allow the measurement of submicron scratches, particles, stains, pits, mounds, handling damage, wear of the carbon layer, outside diameter damage and contamination. This design can also measure the longitudinal Kerr effect by a measurement of the Kerr rotation angle. The advantages of this design are its small size which is made possible by detectors which combine the measurement of phase shift, specular reflectivity, radial and circumferential slope, and scattered light.

Figure 13:
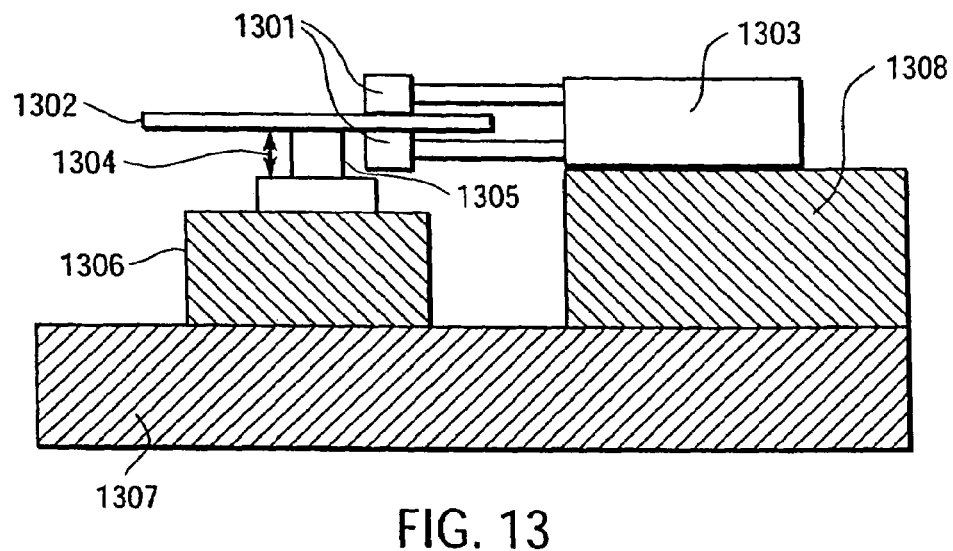
FIG. 13 is an illustration of a final test spindle with dual miniature optical heads and stepper motor according to one embodiment of the present invention.

The miniature optical design may be mounted on the top and bottom of a thin film disk 1302 as shown in FIG. 13 and the resulting combination is translated over the surface of the disk with a stepper or DC servomotor driven stage 1308. A spindle motor 1306 rotates the disk while the optics 1301 is translated in the radial direction so that 100% of the surface of the disk may be measured for defects. The entire apparatus is mounted on a baseplate 1307. The electronics package is located above the stepper motor 1303. The disk is placed upon a vacuum chuck 1305 that is rotated at a high rate of speed.

Figure 14:
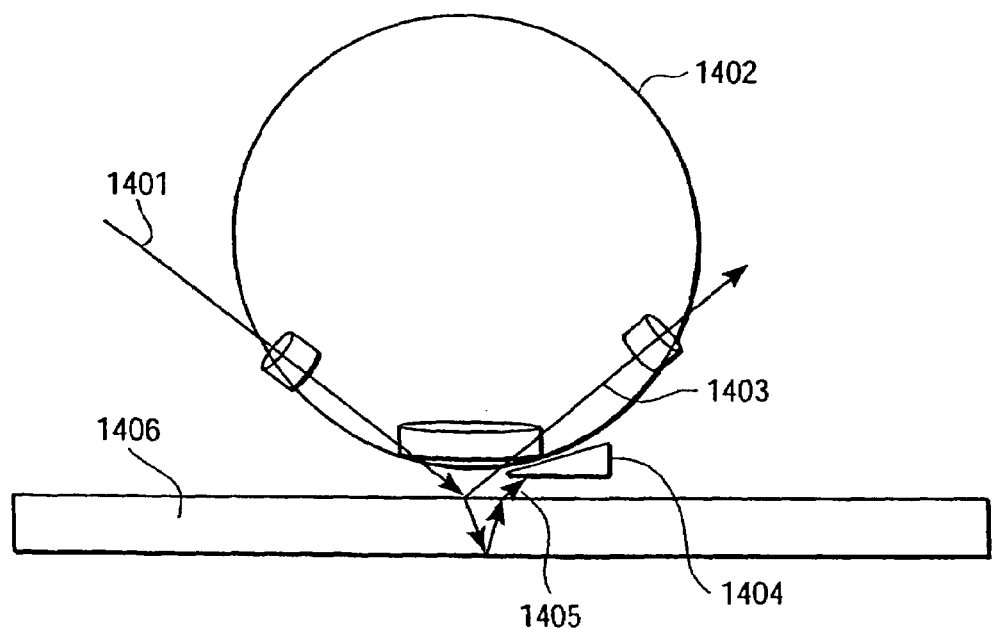
FIG. 14 is an illustration of a spatial filter for blocking bottom surface reflection from a glass substrate according to one embodiment of the present invention.

A problem in the inspection of transparent glass substrates 1406 and other transparent objects is to separate the signal from the top and the bottom surface. This can be accomplished by the use of a spatial filter 1404 that blocks the signal from the bottom surface 1405 and does not affect the top surface reflection 1403. FIG. 14 shows this in the optical design of the Optical Surface Analyzer (OSA). The incoming optical beam is 1401.

The spatial filter 1404 is in the shape of a small wedge that is attached to the bottom surface of the integrating sphere 1402. The location of the spatial filter is adjusted to just block the bottom surface reflection 1405 and not to interfere with the top surface reflection 1403. This invention allows one to separate information from the top and bottom surface of a transparent glass disk or wafer 1406. This invention also works with any transparent medium such as lithium niobate, fused silica, photoresist, and other transparent oxides.

An alternative design does not require the spatial filter to be attached to the bottom of the integrating sphere. For example, the integrating sphere may be omitted and the spatial filter may be attached to any other point on the optical body. The crucial point is that the spatial filter must be located near enough to the transparent substrate so that the reflections from the top and bottom surface are separated in the lateral plane. In this manner it is possible to intercept the bottom surface reflection with the spatial filter and leave the top surface reflection unaffected.

A problem in the measurement of semiconductor wafers is the detection of defects caused by the CMP (Chemical Mechanical Polishing) process. These defects can be residual copper, nitride, slurry, particles, scratches and stains. The measurement is complicated by the fact that the semiconductor wafers have a very complex pattern on their surface. The object is to separate the defects from the complex pattern of semiconductor devices on the surface of the semiconductor wafer. This can be accomplished by the design shown in FIG. 15. The device includes a means for measuring the phase shift between the P and S polarization components of the incident beam and a means to measure the topography of the surface. The device includes a laser 1501 and a polarizer 1502. The laser is directed onto a focusing lens 1503 and onto a mirror 1504 that directs the beam onto a wafer or disk 1505 that may be rotated by a motor 1506. The reflected beam is directed by another mirror 1507 onto a collimating lens 1508 and through a quarter wave plate 1509. The signal passing through the quarter wave plate is directed onto a polarizing beam splitter 1511 that is oriented at 45° to the plane of incidence. The split beams are measured with two photodetectors 1510 and 1512. The phase shift of the incident beam is proportional to the difference in the amplitudes of photodetectors 1510 and 1512.

When the phase shift between the split beams is measured it is found that the orientation of the semiconductor pattern lines will have a substantial effect on the measured phase shift. What is desired is to remove the semiconductor pattern and enhance the defects. A means to accomplish this is to image the wafer with two orthogonal beams as shown in FIG. 16. An optical path shown in FIG. 15 generates each of the beams shown in FIG. 16. Laser one 1601 and detector one 1602 in FIG. 16 generate a phase shift image of the surface that has one particular amplitude due to the orientation of the semiconductor pattern lines. Laser two 1603 and detector two 1604 have a particular amplitude pattern that is identical in lateral shape but opposite in amplitude to that generated by laser one 1601 and detector one 1602. This is because the orientation of the optical beams of lasers one and two are orthogonal with respect to the orientation of the pattern lines. As a result, what is generated are two phase shift images of the surface of the semiconductor that have opposite amplitude phase shift signals from the semiconductor pattern lines. If these two images are added together then the semiconductor pattern will be greatly attenuated. Defects, on the other hand, do not change phase shift in the two orthogonal beams and as a result when the two orthogonal images are added the defects increase in amplitude and the semiconductor pattern diminishes in amplitude. Defects do not have opposite phase shift amplitudes since most defects are isotropic in nature and do not have the strong anisotropy associated with semiconductor pattern lines. This technique effectively enhances the defect signals and diminishes the semiconductor pattern signal. The focused beams 1607 cross at point 1606. The entire device is included within housing 1605.

This invention has the additional advantage that it can simultaneously measure the topography of the surface as has been described in U.S. patent application Ser. No. 09/718, 054 which is incorporated by reference herein in its entirety.

Figure 15:
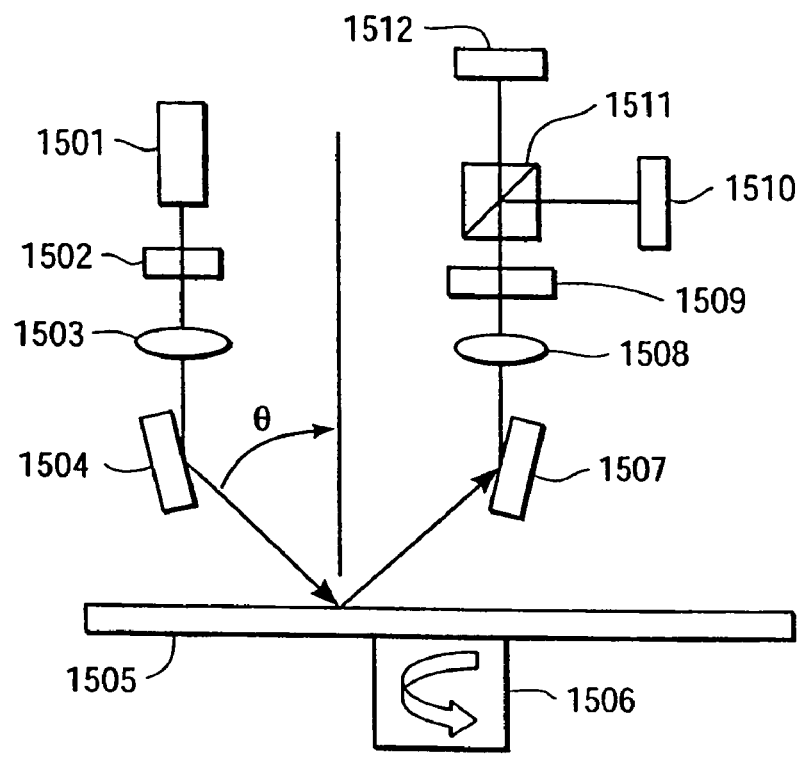
FIG. 15 is an illustration of one half of an optical layout of combined ellipsometer and optical profiler from a side view perspective according to one embodiment of the present invention.
Figure 16:
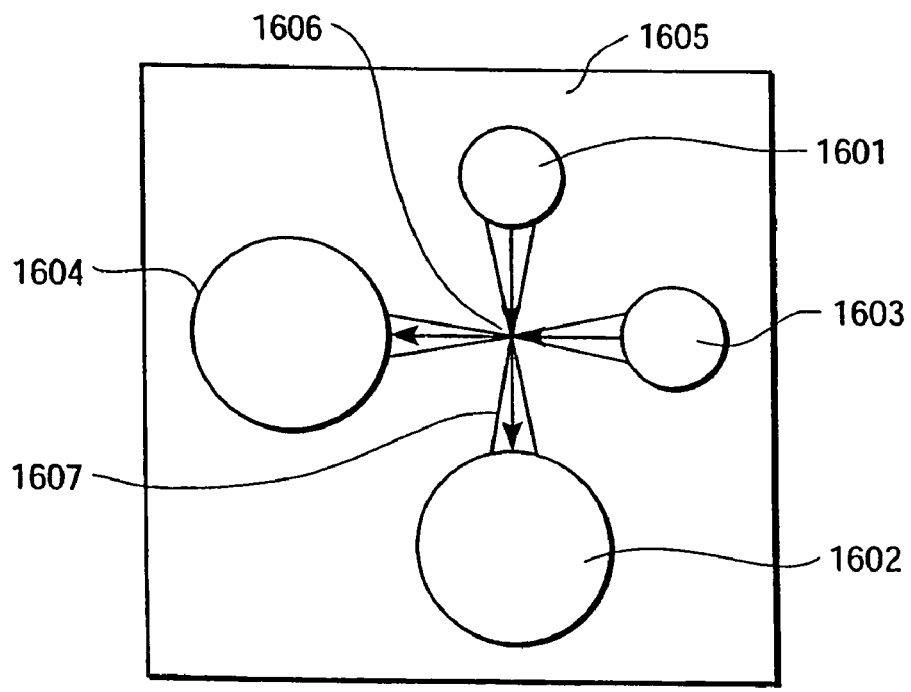
FIG. 16 is an illustration from a top view perspective of a combined ellipsometer and optical profilometer according to one embodiment of the present invention.

In the preferred embodiment the angle of incidence (θ) shown in FIG. 15 is at approximately 60°. Larger or smaller angles of incidence may be used depending upon the application. For example, a larger angle of incidence may be used if a transparent substrate is to be examined. This would be advantageous since a transparent substrate will give a larger signal from the top surface with a greater angle of incidence. Simultaneous measurement at two or more angles of incidence may be accomplished by making the angle of incidence of laser 1601 at a first angle θ1 and that of laser 1603 at a second angle θ2. This will involve changing the angle of the turning mirrors 1504 and 1507 for both lasers 1601 and 1603. The angle of incidence θ1 or θ2 may be between zero and 90 degrees. This particular embodiment allows two angles of incidence to be simultaneously scanned. The simultaneous scanning of additional angles of incidence may be obtained by adding additional lasers in FIG. 16 at angles between the orthogonal pair of lasers 1601 and 1603. Each laser added between 1601 and 1603 may be adjusted to be incident on the surface at any angle of incidence between 0 and 90 degrees.

Simultaneous measurement at two or more wavelengths may be accomplished by making each laser 1601 and 1603 a different wavelength. In this manner phase shift and reflectivity information may be simultaneously collected at two wavelengths. Additional wavelengths may be added by positioning additional lasers and detectors between the orthogonally oriented lasers 1601 and 1603. Each laser added between 1601 and 1603 will have a different wavelength so that any number of wavelengths may be simultaneously incident upon the substrate or disk 1505.

The advantage of multiple wavelengths or angles of incidence is that each angle or wavelength gives different information on the properties of the substrate or disk 1505. For example, shorter wavelengths will allow the detection of smaller particles and thinner films.

Figure 17:
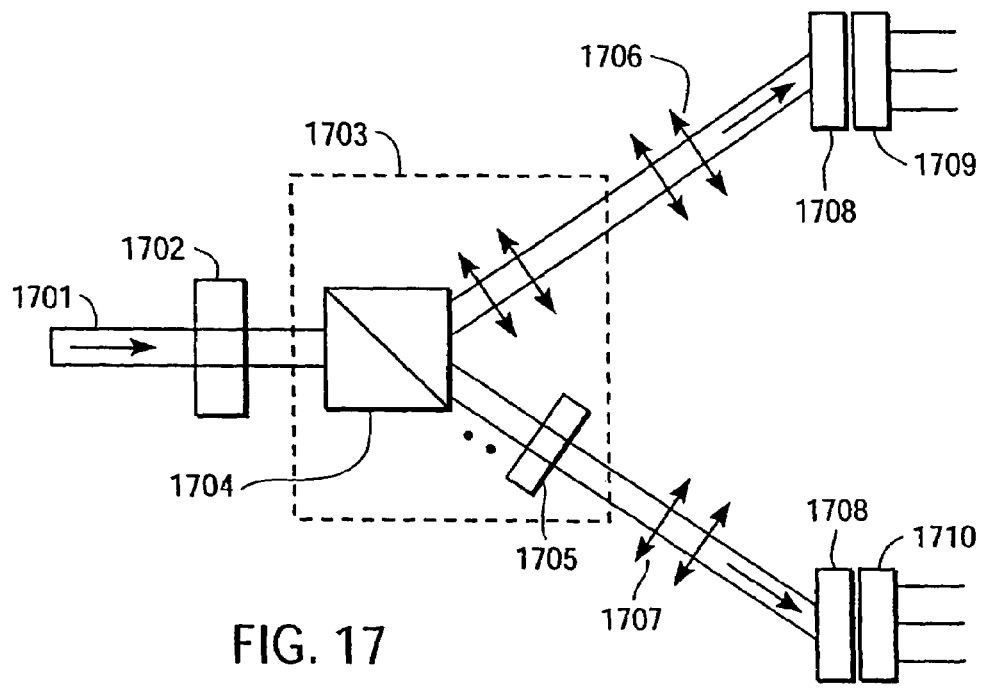
FIG. 17 is an illustration of a system for measuring the phase shift of an elliptically polarized beam by use of a beam splitter that splits the beam into non-orthogonally polarized components according to one embodiment of the present invention.

FIG. 17 illustrates the measurement of the phase shift of an elliptically polarized beam by the use of a beam splitter that splits the beam into non-orthogonally polarized components. The incoming elliptically polarized beam is labeled 1701, this beam is directed into a quarter wave plate 1702 and subsequently into a beam splitter 1703 which splits the beam into non-orthogonally polarized components. Internal to 1703 is a polarizing beam splitter such as a Wollaston prism 1704 or a polarizing cube beam splitter and a polarization rotation device 1705 such as a half wave plate or an optically active quartz polarization rotator. The two beams leaving the beam splitter 1703 are polarized in the same direction as indicated by 1706 and 1707. In general the two beams leaving the beam splitter 1703 may be polarized at any angle with respect to the other. This is accomplished by rotating a half wave plate 1705 (which is internal to the beam splitter 1703) to an arbitrary angle so that the beam leaving 1707 will now be polarized at an arbitrary angle with respect to beam 1706. After the beams leave the beam splitter 1703 they strike diffusers 1708 and subsequently are detected by photodetectors 1709 and 1710. The advantage of this type of beam splitter 1703 is that the outgoing beams may be polarized in the same direction. As a result when the beams 1706 and 1707 strike the diffusers 1708 and photodetectors 1709 and 1710 the reflection from these surfaces will be identical and the detected signals will have identical reduction due to surface reflection. This fact makes the calibration of the instrument considerably easier. The computation of the phase shift of the incoming beam 1701 is proportional to the difference in the amplitude of the two beams as measured by the photodetectors 1709 and 1710.

The incoming laser beams discussed in previous paragraphs have been described as P, S or 45° polarized beams. These earlier discussions are preferred embodiments of this invention. It is also possible to illuminate the surface with unpolarized light and detect the resulting reflected signals with the same optical and electronic methods. The resulting detected signals, which use a source of light which is unpolarized, will still give measurements of the phase shift, topography, reflectivity, defects and particles.

Figure 18:
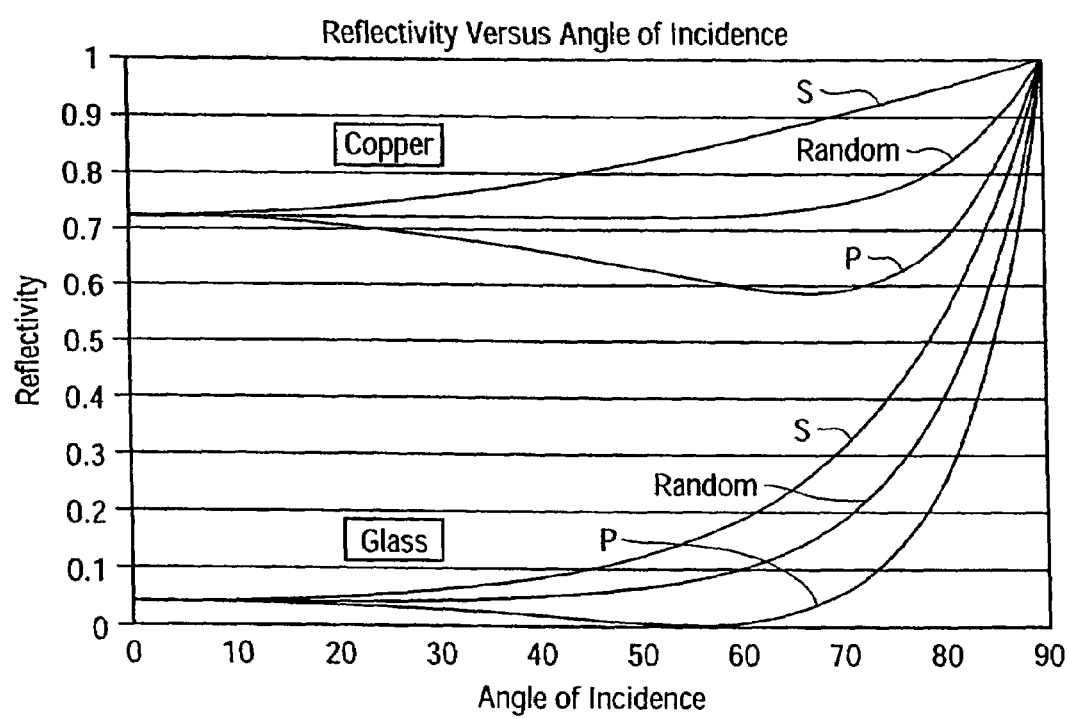
FIG. 18 is a graph illustrating the reflectivity versus angle of incidence for copper and glass with polarization as a parameter according to one embodiment of the present invention.

A problem with conventional optical profilometers is that they are material (reflectivity) dependent. That is, a step height including chrome on a glass substrate will give a different optically measured height than the same step height of chrome on a chrome substrate. One embodiment of the present invention removes this limitation. A reason that the optical profilometer shown in FIGS. 3-6 is material dependent is shown in FIG. 18. FIG. 18 shows the reflectivity versus angle for copper and glass for S, P and randomly polarized light. When a laser beam is focused onto a glass sample the beam will include a range of angles whose magnitude will depend upon the numerical aperture of the focusing lens. If a modest numerical aperture of 0.13 is assumed then the range of angles will be 15°. If the angle of incidence is 58° then the angles incident will vary from 51° to 66°. As a result, the reflected beam will have an intensity variation across its profile given by the reflection coefficient of the material versus angle between 51 and 66° multiplied by the incident intensity variation. For example, in the case of glass the S reflection coefficient varies from 11 to 23% over this range of angles. Copper on the other hand will have an S reflection coefficient variation from 82% to 88% over the same angle range. The net result of this is that the centroid of the beam will be shifted towards larger angles for both copper and glass, but the shift is much greater for glass than for copper. As a result when the focused beam is scanned from glass to copper the centroid of the beam on the quadrant detector will shift showing an apparent height change when in fact there is no change in height.

One way to reduce (but not eliminate) the material (reflectivity) effect is to use randomly polarized light. For this discussion, randomly polarized light is equivalent to circularly or 45° linearly polarized light. FIG. 18 shows that randomly (or circularly or 45° linear) polarized light has much less variation with incident angle when the angle of incidence is less than 45°. As a result the effect of material (reflectivity) may be reduced in designs which would otherwise show a strong reflectivity dependency by using an angle of incidence (θ) which is less than 45° together with light which is randomly, circularly or 45° linearly polarized. If the above criteria are applied to the designs shown in FIGS. 3-6, 27, 28, 29 and 31 then the material (reflectivity) dependency will be reduced.

The embodiments shown in FIGS. 19 through 26 completely remove the material (reflectivity) dependency by the use of a retro-reflector. The embodiments shown in FIGS. 19 and 20 include an S polarized laser diode 1901 which is split by a 50/50 non-polarizing beam splitter 1903 and directed onto a focusing lens 1904 which focuses the beam 1906 to a small spot on a substrate 1907 which may be a silicon wafer, thin film disk or optical substrate. The beam reflects from the substrate and is recollimated by a second lens 1904 and then reflects from a retro-reflector 1905. The retro-reflector 1905 may be a conventional retro-reflecting prism (a Porro prism) or a conventional cube corner prism which are both available from CVI, Inc. Albuquerque, N. Mex.

The retro-reflected beam is then refocused upon the substrate and reflects a second time and then passes to the quadrant detector 1902 where the height and slope are measured. The double reflection from the substrate removes the material dependency from the optical signal. The retro-reflector takes the first reflection from the surface and inverts the beam profile and reflects it back to the surface where it undergoes a second reflection. The second reflection alters the beam profile in exactly the opposite manner of the first reflection, since the beam profile has been inverted by the retro-reflector. As a result the doubly reflected beam has a symmetric profile and its centroid is not shifted regardless of the material type, reflectivity, polarization, angle of incidence or range of angles in the beam. However, if there is a height change present then the amount of height change will be doubled by the retro-reflector.

Figure 34:
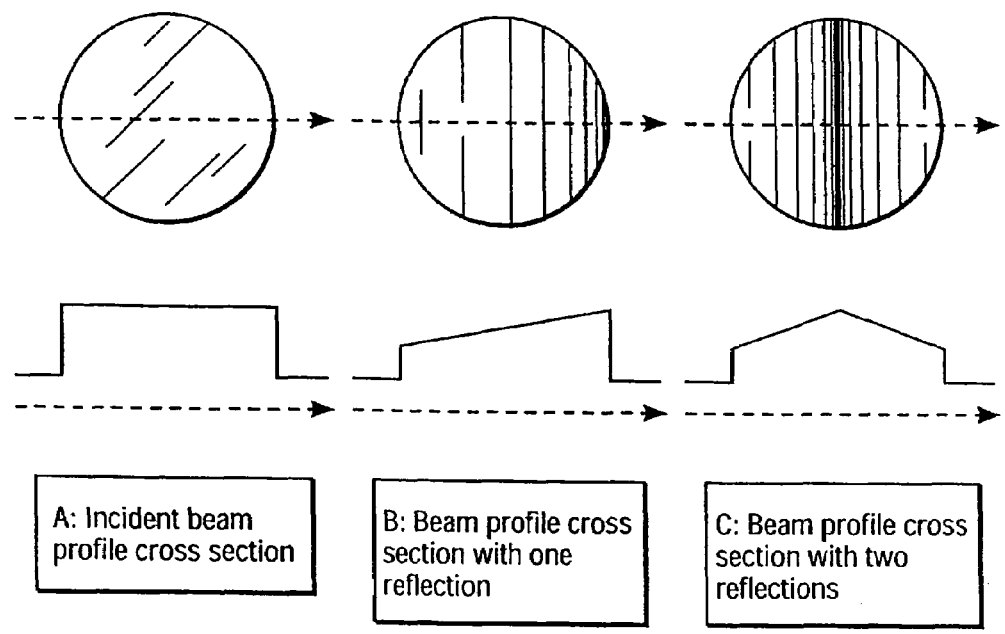
FIG. 34 is an illustration depicting the beam profiles after one and two reflections from the surface under measurement according to one embodiment of the present invention.

A change in the beam profile with reflection from a surface is shown in FIGS. 34A-34C. In FIG. 34A a uniform beam profile has been chosen for illustrative purposes. In an actual device the beam profile would have a Gaussian shape. After one reflection from the surface under investigation the portion of the beam coming from larger angles of incidence (on the right in FIG. 34B) will have a greater intensity as shown by the profile illustrated in FIG. 34B. It is the non-uniform intensity shown in FIG. 34B which results in a centroid shift of the beam even in the absence of any height change. When the beam strikes the retro-reflector the profile is inverted and redirected towards the surface where it undergoes a second reflection. The second reflection produces the symmetric beam profile shown in FIG. 34C. The symmetric beam profile produced by the two reflections and the retro-reflector does not have a centroid shift when there is no height change regardless of the material from which the beam is reflecting.

Figure 20:
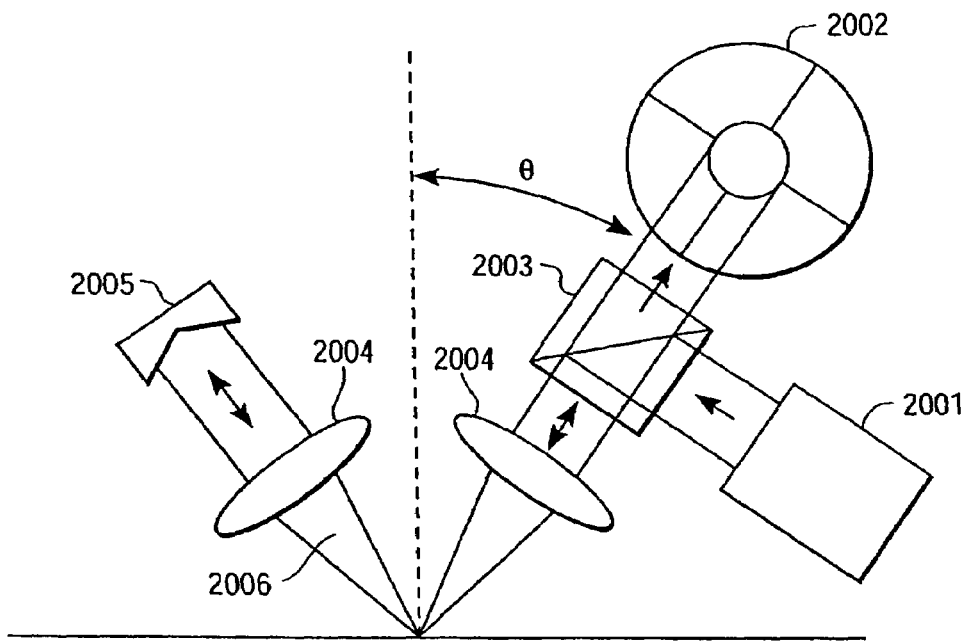
FIG. 20 is an illustration of another half of a material independent optical profilometer from a side view perspective according to one embodiment of the present invention.
Figure 22:
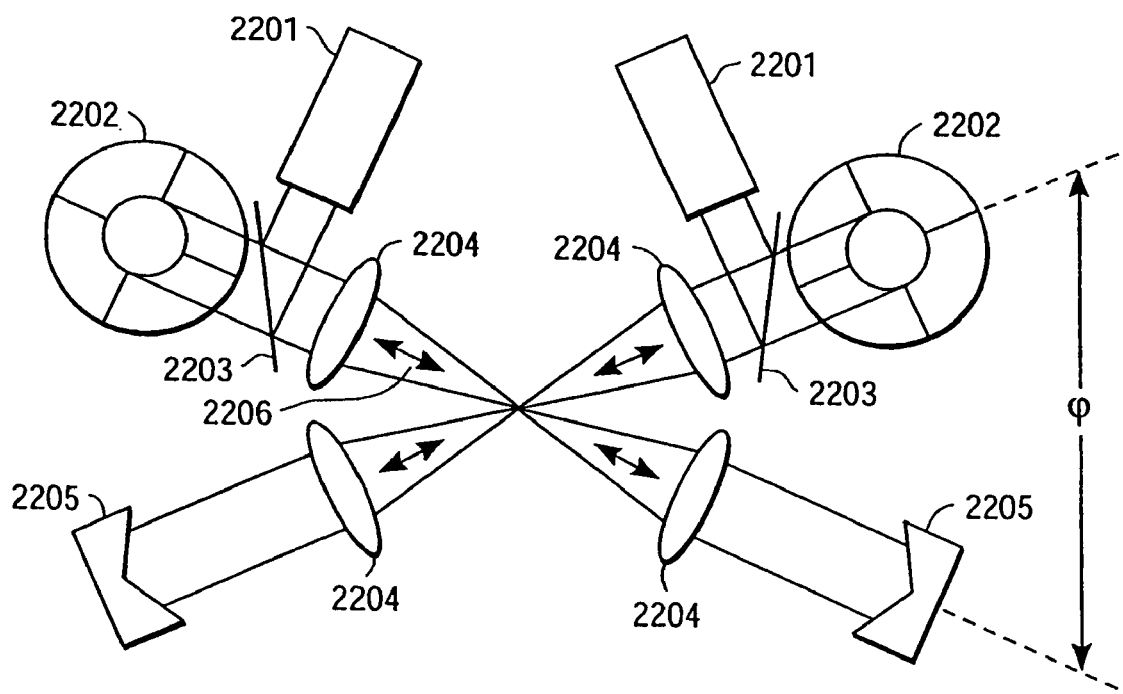
FIG. 22 is an illustration having a top view perspective of an optical profilometer that is completely material independent according to one embodiment of the present invention.

Using a second optical head that is mirror imaged about the focal point, as shown in FIG. 20, allows the separation of the slope and height. In FIG. 20, 2001 is the S polarized laser diode, 2002 the quadrant detector, 2003 the 50/50 non-polarizing beam splitter, 2004 the focusing lenses, 2005 the retro-reflector and 2006 the focused beam. When these optical heads are combined as shown in FIG. 22 and the outputs are added, the slope signals will cancel and the height signals will add. In FIG. 22 2201 are the S polarized lasers, 2202 the quadrant detectors, 2203 the 50/50 non-polarizing beam splitters, 2204 the focusing and collimating lenses, 2205 the retro-reflectors. The separation angle $\phi$ is generally set to be less than 10°. The quadrant detectors may be replaced with bi-cell detectors with the split-oriented perpendicular to the plane of incidence.

The sensitivity is increased by using a higher angle of incidence, the retro-reflector and adding the outputs of the mirror imaged heads together. Theoretically the sensitivity can be increased to 8 times the actual surface height. This would require an incidence angle of 9020, in practice one can get a sensitivity increase of 6.9 by using an incidence angle of 60° with retro-reflectors and summing two mirror images heads. This results in an optical profilometer that can achieve high lateral resolution, high sensitivity, measure 90° step heights, is material independent and separates the slope and height signals.

Figure 19:
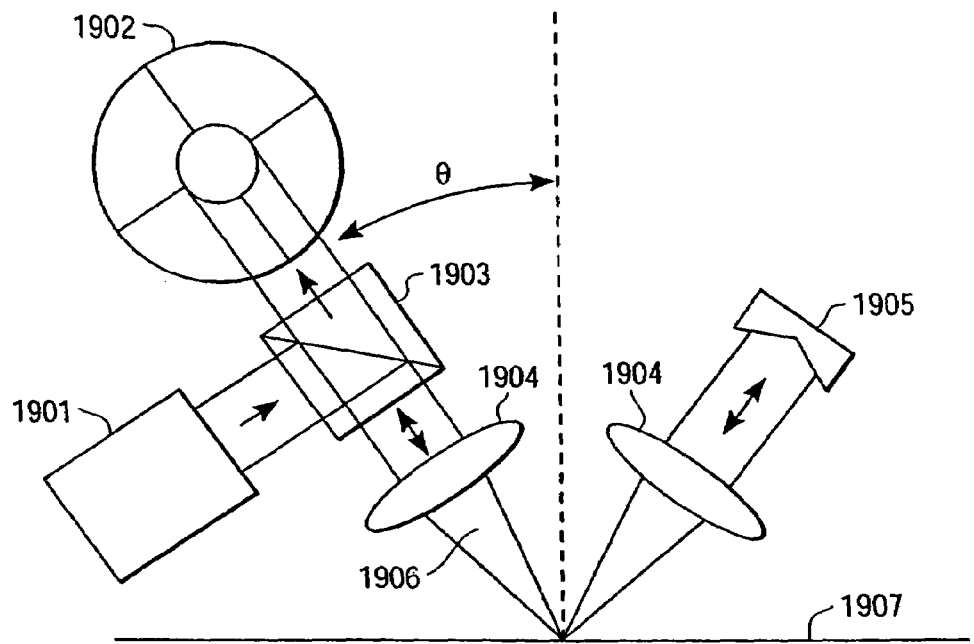
FIG. 19 is an illustration of one half of a material independent optical profilometer from a side view perspective according to one embodiment of the present invention.
Figure 21:
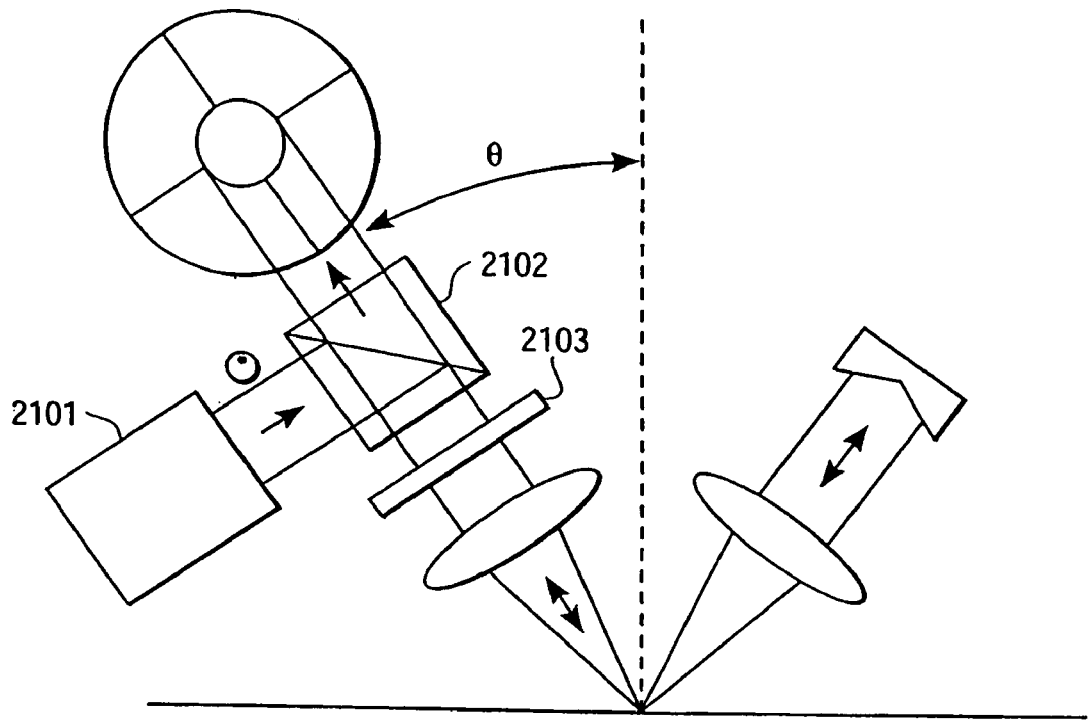
FIG. 21 is an illustration of one half of a material independent optical profilometer that uses incident light that is circularly polarized according to one embodiment of the present invention.

An alternate embodiment to the design shown in FIG. 19 is given by FIG. 21. This design uses an S polarized laser 2101 that is directed onto a polarizing beam splitter 2102. The S polarized beam is completely reflected by the polarizing beam splitter and passes through a quarter wave plate 2103 which is oriented such that circularly polarized light is focused onto the substrate. The circularly polarized light is retro-reflected and passes through the quarter wave plate 2103 a second time at which point it becomes P polarized and passes through the polarizing beam splitter without reflection and impinges upon the quadrant detector. This design is much more optically efficient than that shown in FIG. 19 and no beam reflects back towards the laser 2101. The disadvantage of this design is that the signal reflected from the surface for circularly polarized light is less than for S polarized light. The design shown in FIG. 21 may be used to replace the elements in FIG. 22 so that an optical profilometer that uses circularly polarized light is created.

Figure 23:
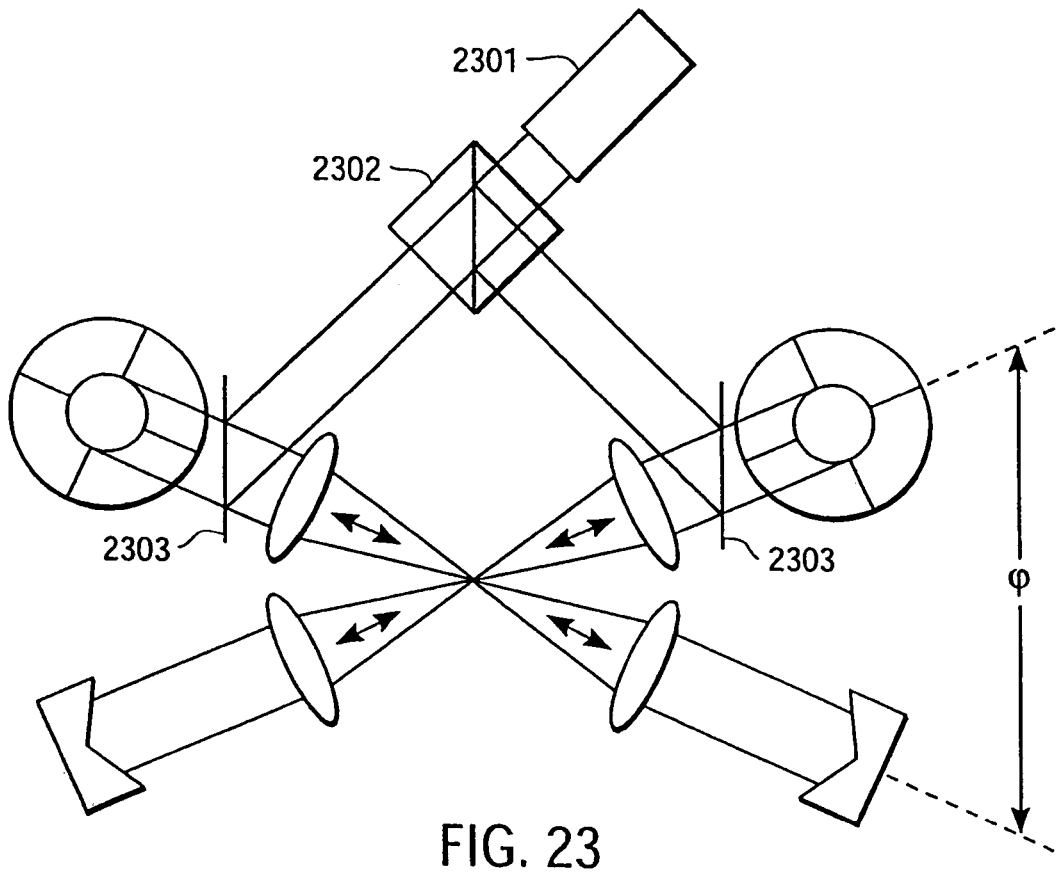
FIG. 23 is an illustration having a top view perspective of a material independent optical profilometer using a single laser as its optical source according to one embodiment of the present invention.

Another embodiment of a material independent optical profilometer is shown in FIG. 23. This embodiment uses a single S polarized laser diode 2301 and a 50/50 non-polarizing beam splitter 2302. The split beams are directed onto a pair of 50/50 non-polarizing beam splitters 2303 and then focused upon the substrate. The advantage of this design is that it uses a single laser diode. This design may also use the circularly polarized elements shown in FIG. 21.

Figure 24:
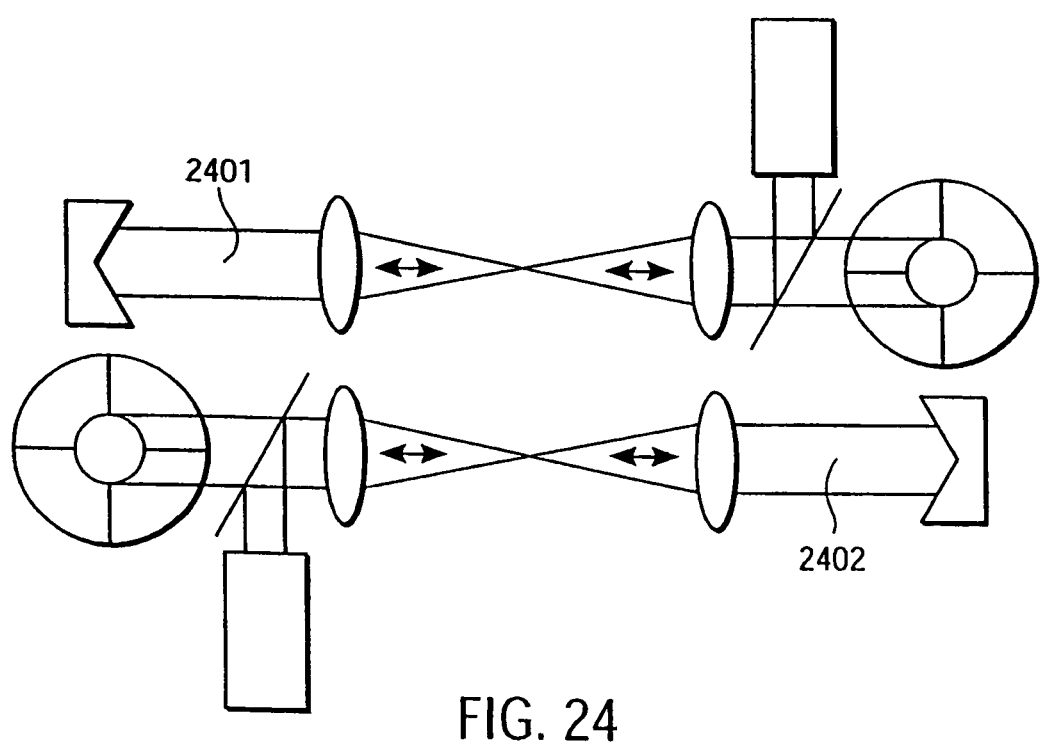
FIG. 24 is an illustration having a top view perspective of an optical profilometer that is completely material independent according to another embodiment of the present invention.

FIG. 24 shows another embodiment of a material independent optical profilometer. This design is similar to FIG. 22 but in this case the beams do not overlap. The individual elements 2401 and 2402 are mechanically attached together and scanned over a substrate at the same time. The resulting two images are aligned with software in order to account for the difference in the position of the two beams on the substrate. Once the beams have been aligned in software the images are added so that slope and height may be separated as discussed in earlier paragraphs. This design may also use the circularly polarized elements shown in FIG. 21.

Figure 25:
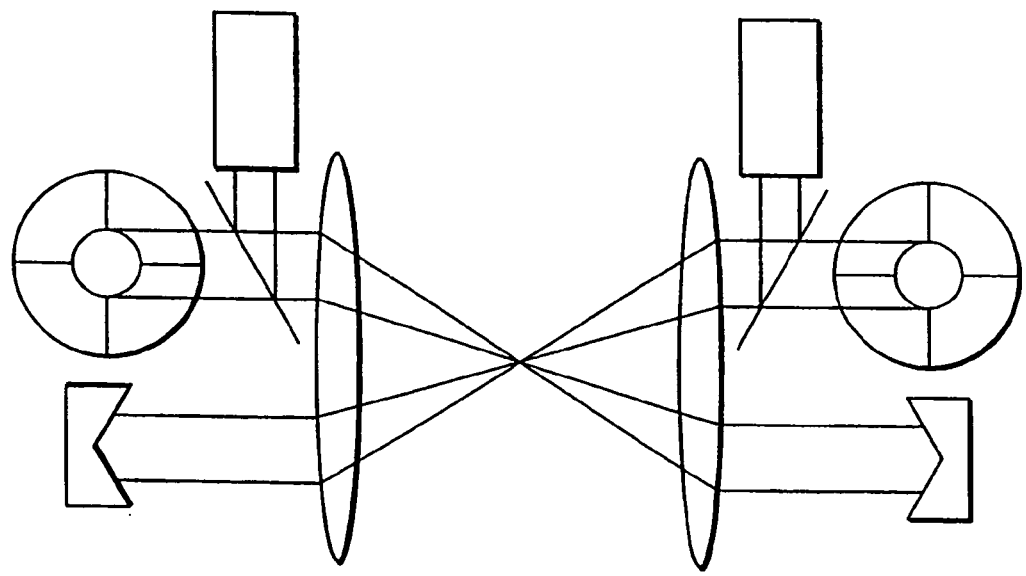
FIG. 25 is an illustration having a top view perspective of an optical profilometer that is completely material independent according to another embodiment of the present invention.

FIG. 25 shows another embodiment of an optical profilometer that separates slope and height and is material independent. This design uses only two lenses instead of the four used in FIGS. 22, 23 and 24. The advantage of this design is that it uses fewer optical components. This design may also use the circularly polarized elements shown in FIG. 21.

Figure 26:
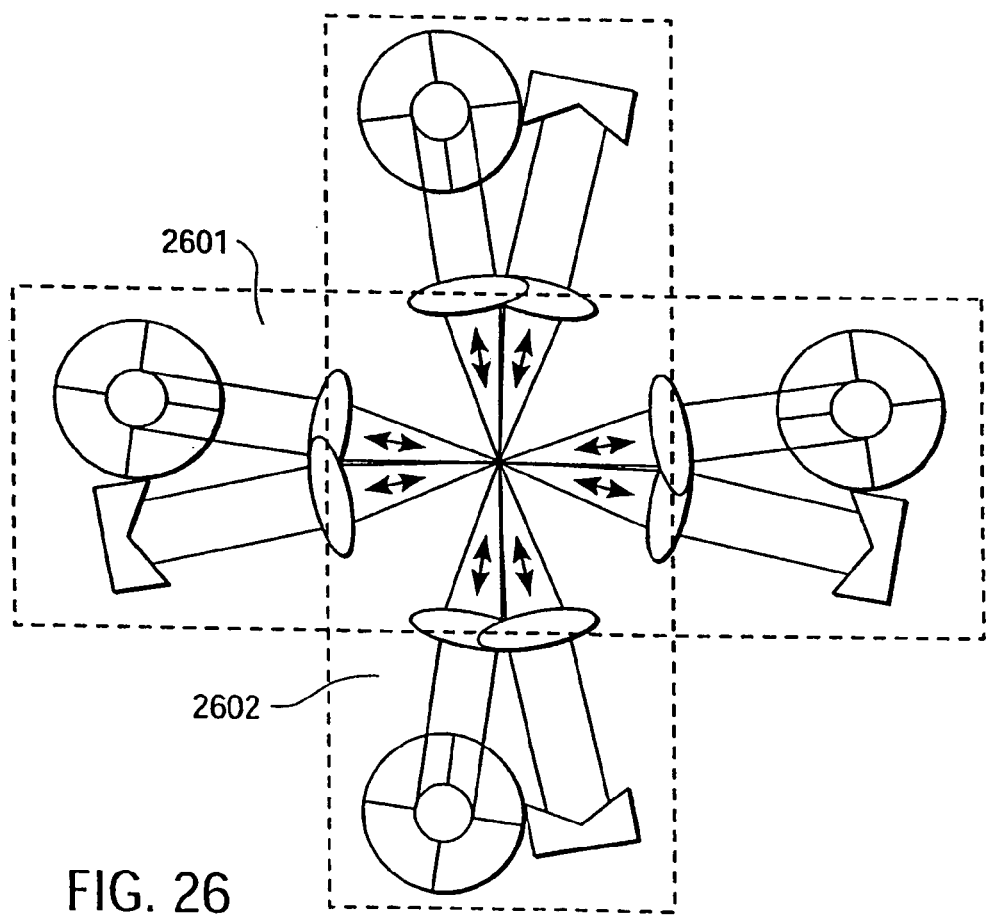
FIG. 26 is an illustration of a pair of material independent optical profilometers that are arranged at 90° to cancel pattern effects on patterned semiconductor wafers according to one embodiment of the present invention.

FIG. 26 shows a profilometer design that is used to eliminate the effects of the semiconductor pattern. When a patterned semiconductor wafer is rotated beneath a fixed beam whose plane of incidence is oriented in the radial or circumferential direction as shown in FIG. 4, artifacts will be created in the data which are dependent upon the orientation of the semiconductor pattern. These effects may be eliminated by the design shown in FIG. 26 that includes a circumferentially oriented profiler 2601 and a radially oriented profiler 2602. If both these heads are used to simultaneously scan the surface of the patterned wafer and then the separate outputs from 2601 and 2602 are added together then the resulting data will be independent of the pattern on the semiconductor wafer. This design may also use the circularly polarized elements shown in FIG. 21.

Another problem with conventional optical profilometers is that they may give incorrect results when attempting to measure steps or profiles on thin transparent layers. This is because the bottom surface reflection from the thin transparent layer gives a spurious signal that is added to the signal from the top surface. This problem can be solved by using a deep UV wavelength (for example 266 nm) for the laser in FIG. 19 (1901) where nearly all transparent materials are strongly absorbing. If a deep UV laser is used then there will be no bottom surface reflection since the thin transparent layer will absorb the UV signal. An additional advantage of using a 266-nm laser is that it can be focused to a beam size of approximately 0.2 microns resulting in a lateral resolution of 2000 □.

Figure 27:
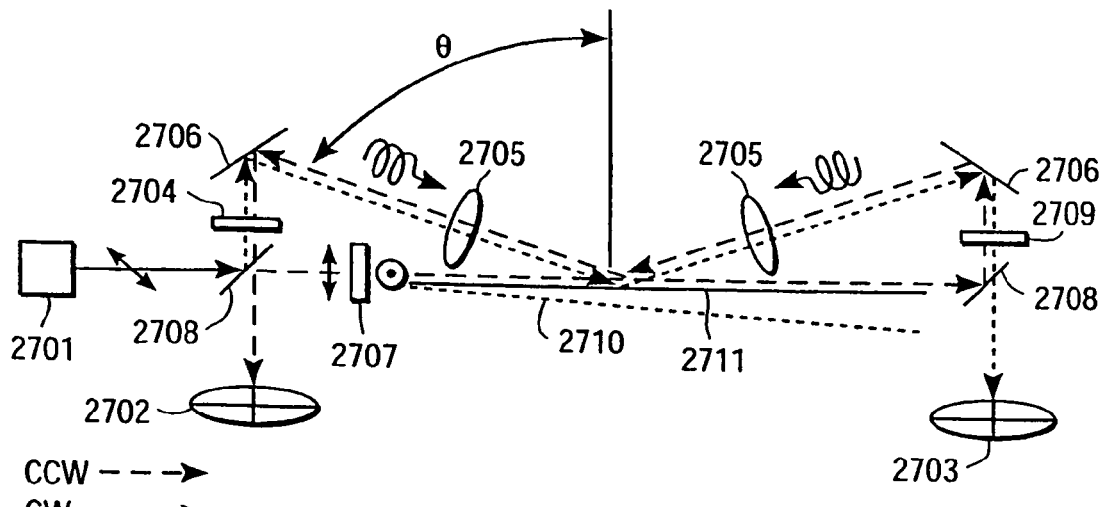
FIG. 27 is an illustration of an optical profilometer that cancels slope and measures height using circularly polarized light incident upon a sample according to one embodiment of the present invention.

FIG. 27 shows an optical profiler design that also separates slope and height. This design will be sensitive to material (reflectivity) changes but these effects can be minimized by choosing an incidence angle less than 45°, operating with a modest numerical aperture and using random, circular or 45° linear polarization, as discussed earlier. This embodiment begins with a random, circular or 45° linearly polarized (as shown) laser 2701 that is incident upon a polarizing beam splitter 2708. The P component is transmitted and is rotated to S polarization by the half wave plate 2707. This counter clockwise propagating beam continues to the right and totally reflects from polarizing beam splitter 2708 and passes through a quarter wave plate 2709 which is oriented to produce circularly polarized light which is directed onto the substrate 2711 by a turning mirror 2706. A lens 2705 focuses the beam and after reflecting it is recollimated by a second identical lens 2705. The beam then is directed onto a second turning mirror 2706 and passes through a second quarter wave plate 2704 which is oriented to produce P polarization. The P polarized beam passes through the polarizing beam splitter 2708 and impinges upon the quadrant detector 2702. A similar path is followed by the clockwise propagating beam with this beam impinging upon the right quadrant detector 2703.

When the substrate 2711 changes slope as indicated by 2710 the clockwise (CW) and counter clockwise (CCW) beams will move in the same direction on the detectors 2702 and 2703. For the slope change shown with 2710 both CW and CCW beams will move to the right on detectors 2702 and 2703. When there is a height change then the CW and CCW beams will move in opposite directions on the detectors 2702 and 2703. For example, if the substrate plane 2711 moves up then the CCW beam on 2702 will move to the right and the CW beam will move to the left on 2703. As a result, if the outputs of 2702 and 2703 are subtracted the slope signals will cancel and the height signals will add. This design will be insensitive to slope changes and will have double the height sensitivity.

Figure 28:
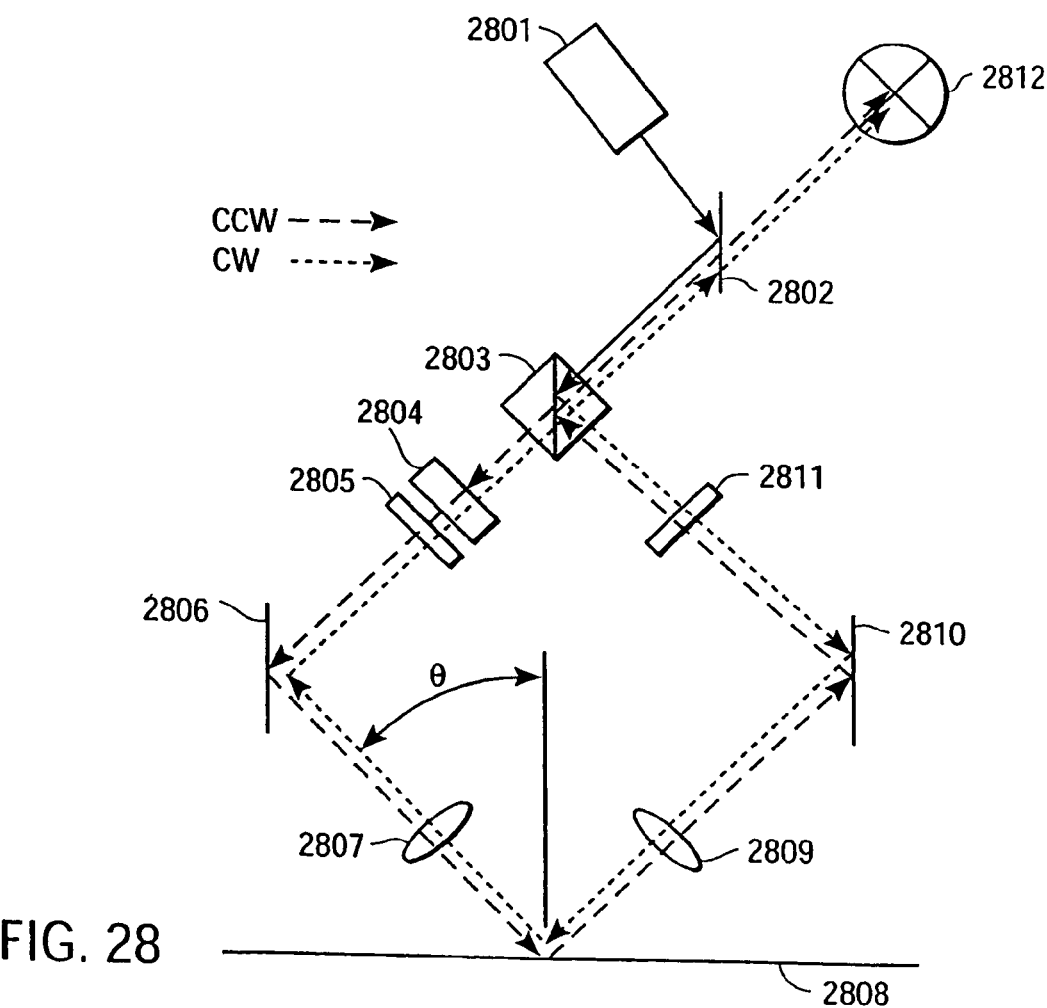
FIG. 28 is an illustration of an optical profilometer that cancels slope and measures height using a single detector and using S polarized light incident upon a sample according to one embodiment of the present invention.

FIG. 28 shows another embodiment of an optical profilometer that separates slope and height. This design will be sensitive to material (reflectivity) changes but these effects can be minimized by choosing an incidence angle less than 45°, operating with a modest numerical aperture and using random, circular or 45° linear polarization, as discuss earlier. This design begins with a 45° linearly polarized laser 2801 that is directed onto a 50/50 non-polarizing beam splitter 2802. The reflected beam is directed onto a polarizing beam splitter 2803. The polarizing beam splitter 2803 may be a Glan-Thompson or a polarizing cube beam splitter or any similar polarizing beam splitter. The split beam is separated into a P polarized component which propagates counter clockwise (CCW) and an S polarized component which propagates clockwise (CW). The P polarized CCW beam is rotated by a half wave plate 2804 so that it becomes S polarized and then any remaining non S polarized intensity is removed by an S oriented polarizer 2805. The CCW beam is directed onto a focusing lens 2807 by a turning mirror 2806 and is reflected from the substrate 2808. The CCW beam is recollimated by another identical lens 2809 and reflects from another turning mirror 2810 and passes through another S polarizer 2811 and then reflects from the polarizing beam splitter 2803. The resulting beam is directed to the beam splitter 2802 and a portion passes through and impinges upon the quadrant detector 2812. The quadrant detector may be replaced with a bi-cell detector with the split perpendicular to the plane of incidence.

The CW propagating beam follows a path similar to the CCW beam after reflecting from the beam splitter 2803. After the CW beam reflects from the substrate 2808 and passes through the polarizing beam splitter 2803 a portion then passes through the non-polarizing beam splitter 2802 and impinges upon the quadrant detector 2812. When the substrate has a slope the CW and CCW beams will move apart (opposite directions) on the detector 2812 and the output will be zero. When the substrate has a height change the CW and CCW beams will move in the same direction on the detector 2812 and the output will be double that of a single beam. The advantage of this design is that it uses a single detector, separates slope and height and gives twice the height signal. There will be no interference of the CW and CCW beams on detector 2812 since they are orthogonally polarized.

Figure 29:
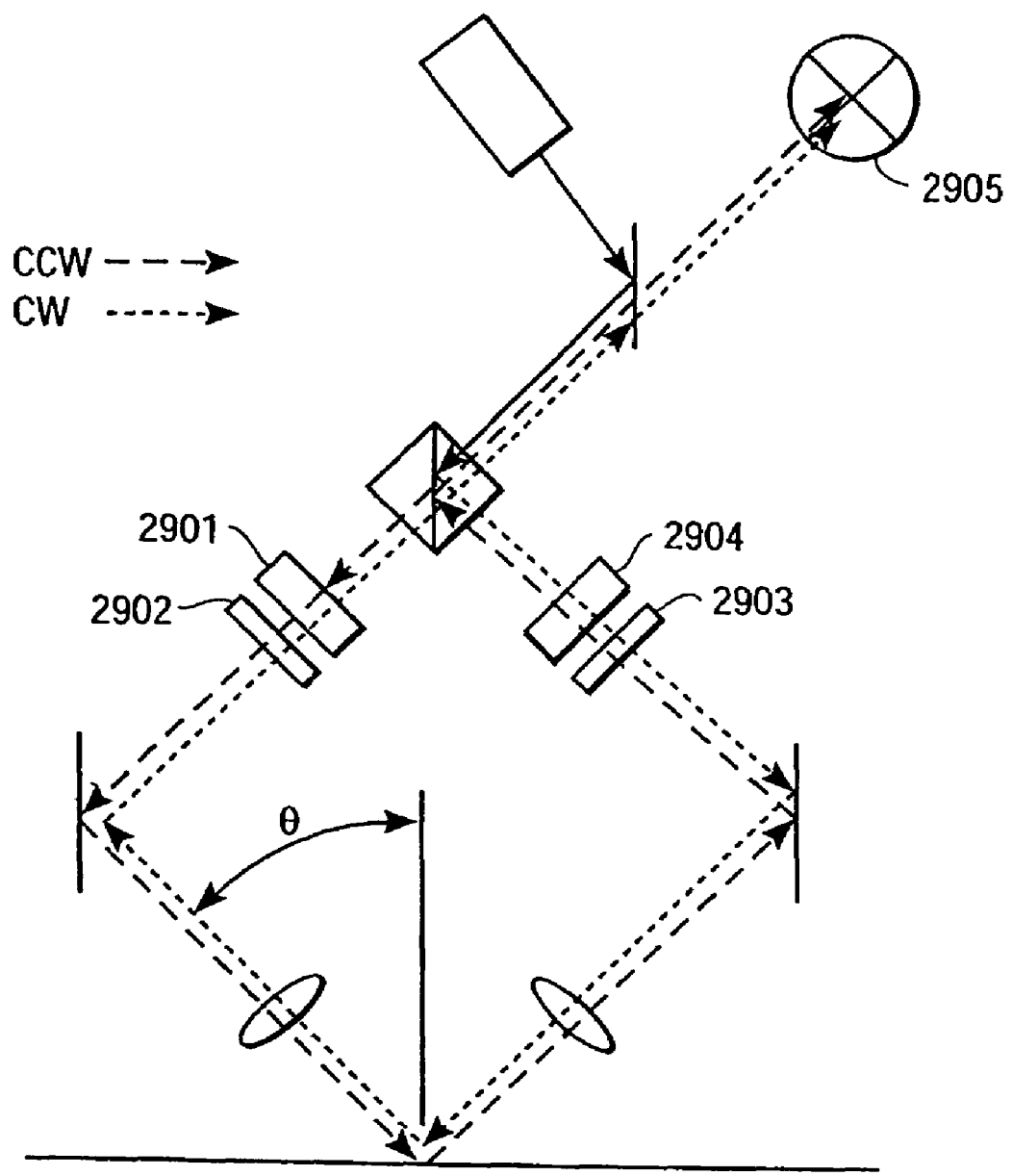
FIG. 29 is an illustration of an optical profilometer that cancels slope and measures height using a single detector and using 45° linearly polarized light incident upon a sample according to one embodiment of the present invention.

FIG. 29 shows another embodiment of an optical profilometer that separates slope and height. This design uses 45° linearly polarized light incident upon the substrate so as to minimize the effects of material differences. The design is similar to that shown in FIG. 28 except the CCW beam encounters a half wave plate 2901 which is oriented to rotate the incident P light by 45° and this light passes through a 45° oriented linear polarizer 2902. Upon reflecting from the substrate the beam passes through a second 45° oriented linear polarizer 2903 and through a half wave plate 2904 which is oriented to rotate the polarization an additional 45° so that it becomes S polarized. The S polarized light reflects completely from the polarizing beam splitter and is directed onto the quadrant detector 2905. If the angle of incidence is set to approximately 30° and the numerical aperture chosen to be about 0.13 then this design will reduce the effects of material differences upon the height signal. The advantages of this design are its double height sensitivity, reduced material sensitivity, separation of height and slope, and single detector.

It is interesting to compare the advantages and disadvantages of the designs shown in FIG. 29 and FIG. 22. FIG. 29 is simpler since it uses a single detector, but it has some material sensitivity. The design of FIG. 29 is limited to relatively small numerical apertures because of material sensitivity whereas that of FIG. 22 may use any numerical aperture and still be material independent. The angle of incidence of the design of FIG. 29 is limited to less than 45° because of material sensitivity. This reduces the sensitivity according to FIG. 7, whereas the design of FIG. 22 does not suffer this sensitivity loss. The retro-reflector on FIG. 22 and the double head design gives a four-fold increase in the height sensitivity. This fact and angle of incidence multiplier mean that the theoretical height sensitivity of the design of FIG. 22 is 8 times the physical height change. The same analysis applied to the design of FIG. 29 gives double the physical height change. In summary, the design of FIG. 22 will be material insensitive, achieves perfect slope cancellation, may be run at much higher lateral resolution, and is 4 times more sensitive than that of FIG. 29. The advantage of the design of FIG. 29 is the simplicity of a single detector. The designs of FIGS. 28 and 29 also achieve perfect slope cancellation since the path length for the CW and CCW beams are identical. There is no interference of the CW and CCW beams on the detector 2905 since the beams are orthogonally polarized.

Figure 30:
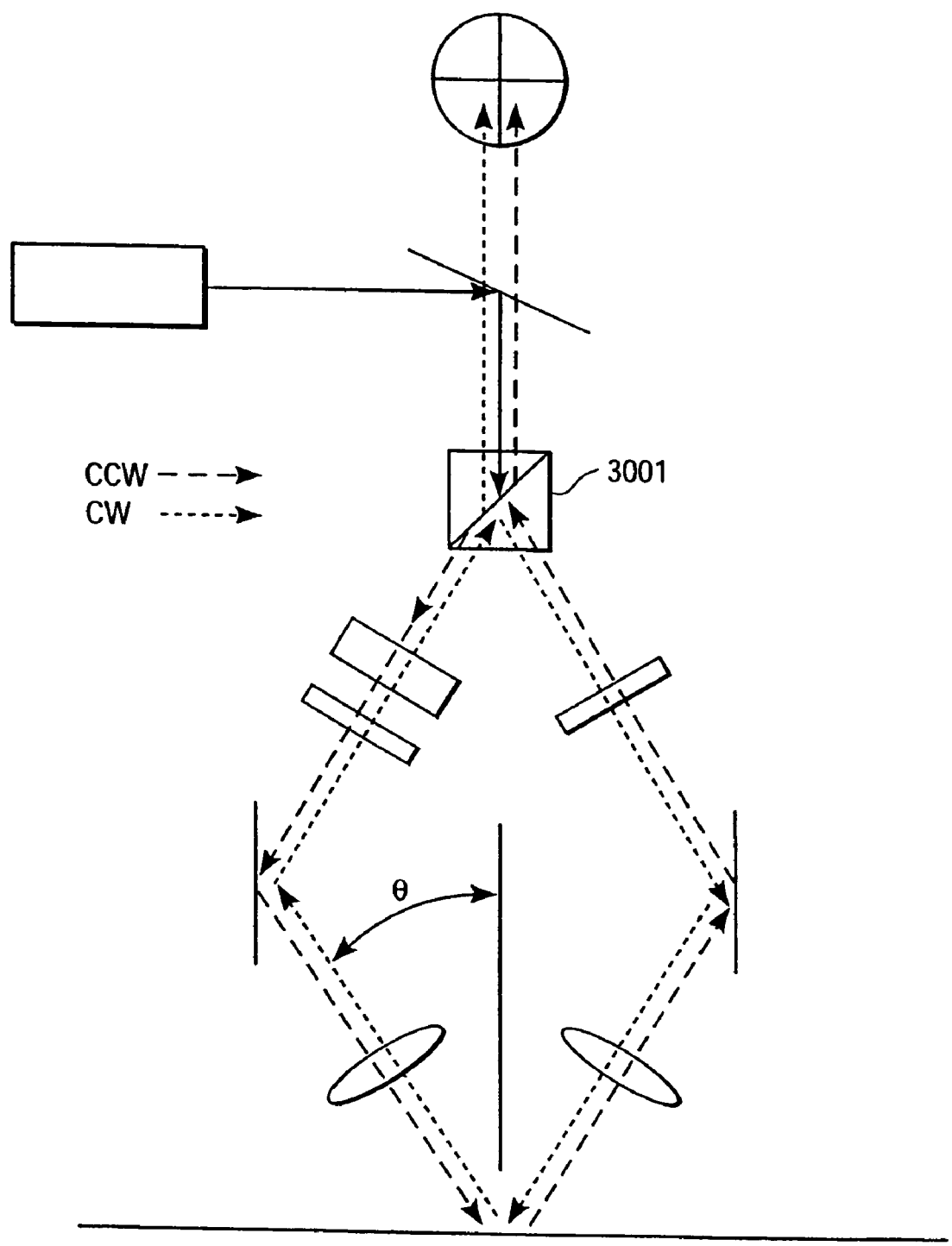
FIG. 30 is an illustration of an optical profilometer that measures only slope and cancels height and material effects according to one embodiment of the present invention.

FIG. 30 shows an optical design that measures only slope and rejects height and material (reflectivity) changes. This design is very similar to that shown in FIG. 28 except in this case a Wollaston prism 3001 acts as a polarizing beam splitter. The orientation of the prism 3001 means that both the CW and CCW beams strike the prism on the same side of the split in the prism. This fact means that any height (or material) changes will move in opposite directions on the detector and slope changes will move in the same direction. As a result this design rejects material sensitivity and height changes and doubles the sensitivity to slope. This design is intended as a high sensitivity slope measurement device. The slope may be integrated to arrive at the topographic profile.

Figure 31:
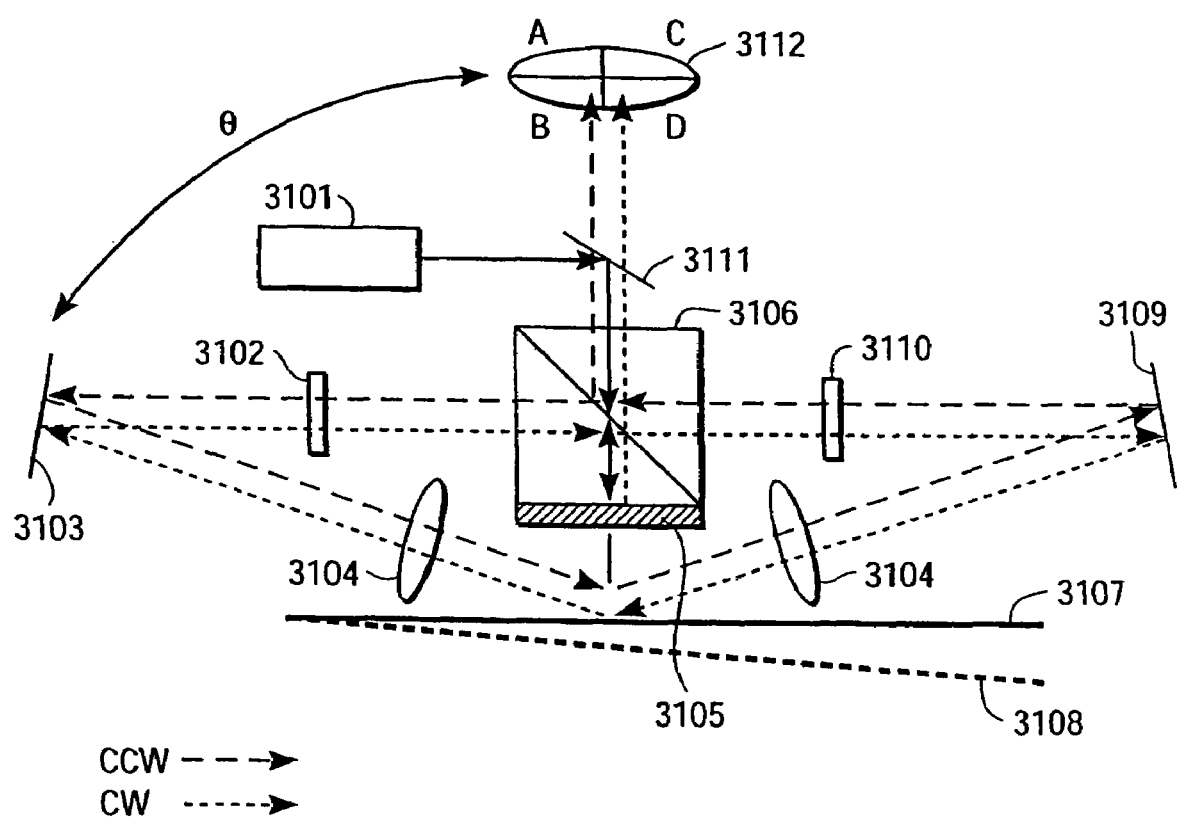
FIG. 31 is an illustration of an optical profilometer that cancels slope and measures height using a single detector and using S polarized light incident upon a sample according to another embodiment of the present invention.

The design shown in FIG. 31 is another embodiment of an optical profiler that measures height and rejects slope. This design will be material (reflectivity) sensitivity. The design as shown uses S polarized light but it is also possible to use random, circular or 45° linearly polarized light, for example. If one of these polarization's are used and the angle of incidence θ is less than 45° then the material sensitivity will be reduced. The design begins with a 45° linearly polarized laser 3101 which is directed onto a 50/50 non-polarizing beam splitter 3111 which directs a portion of the beam to a polarizing beam splitter 3106. The splitter 3106 reflects the S portion of the beam and directs it in the clockwise direction where it passes through a S polarizer 3110 (to improve the linear polarization) and is deflected onto a substrate 3107 by a turning mirror 3109. The CW beam is focused by a lens 3104 and recollimated by an identical lens 3104 after reflecting from the substrate 3107. The CW beam is deflected by a turning mirror 3103 and passes through another S polarizer 3102 and impinges upon the polarizing beam splitter 3106 and is reflected downward onto a quarter waveplate/mirror combination 3105 which converts the S polarization to P which reflects from 3105 and passes through the polarizing beam splitter 3106 and a portion passes through 3111 and impinges upon the quadrant detector 3112. The CCW propagating beam follows a similar path before impinging upon the quadrant detector 3112. A bi-cell detector may be substituted for the quadrant detector 3112 with the split-oriented perpendicular to the plane of incidence.

The embodiment shown in FIG. 31 behaves in a manner similar to those embodiments shown in FIGS. 28 and 29. When the CW and CCW beam encounter a slope 3108 in the substrate the beams move apart on the detector 3112. When a height change is encountered then the CW and CCW beams move in the same direction on the detector 3112. As a result slope changes are cancelled and height changes are doubled. The advantage of this design is that it uses a single detector. This embodiment achieves nearly complete slope cancellation since the CW and CCW beam paths differ only by the length of the polarizing beam splitter 3106. There is no interference of the CW and CCW beams on the detector 3112 since they are orthogonally polarized.

Figure 32:
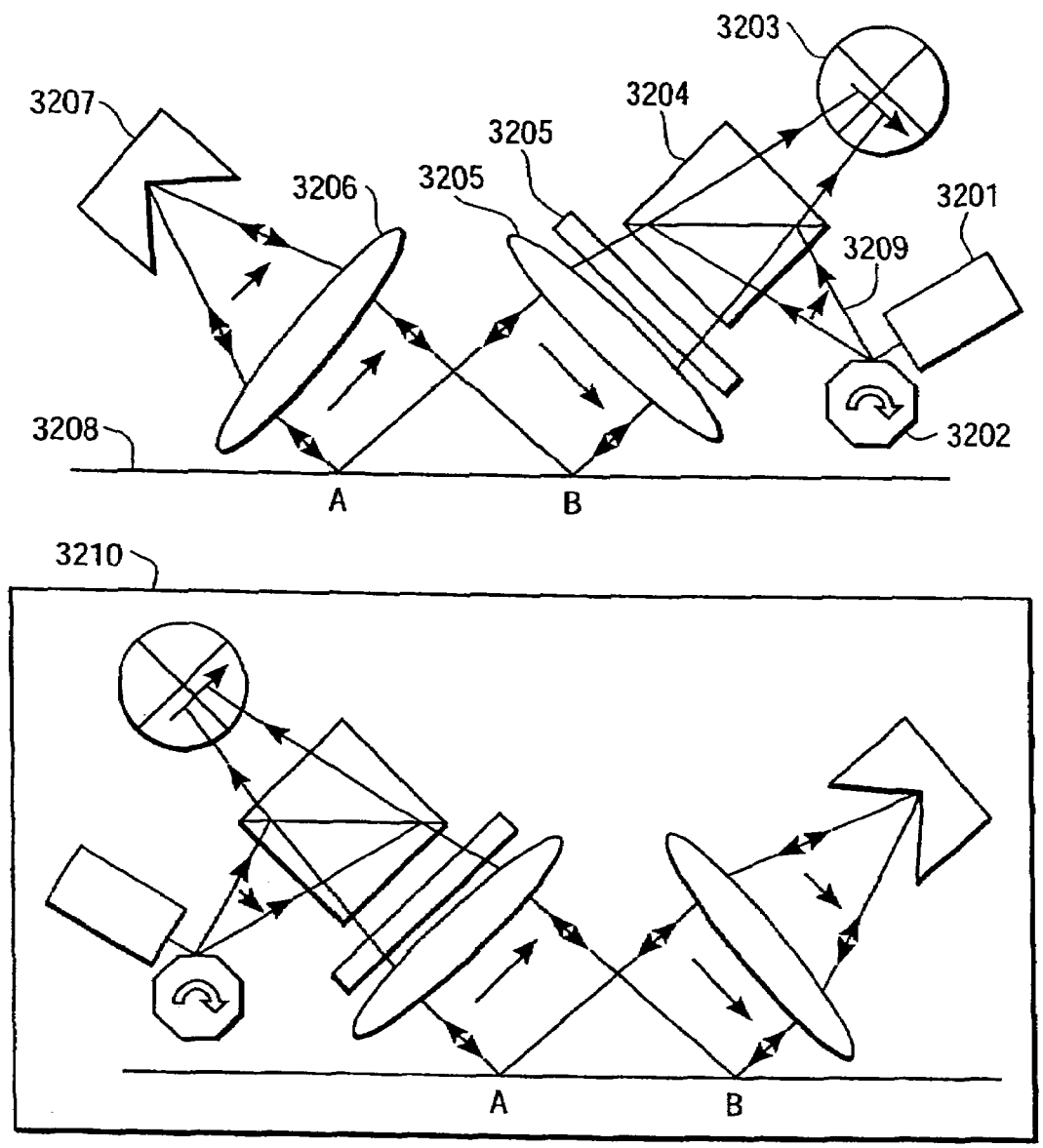
FIG. 32 is an illustration having a side view perspective of an optically scanned version of a material independent optical profilometer shown in FIGS. 19, 20, 21 and 22 according to one embodiment of the present invention.

FIG. 32 shows an optically scanned embodiment of a material independent optical profilometer. This embodiment uses a rotating polygon 3202 (available from Lincoln Laser, Phoenix, Ariz.) or XY galvanometric scanner (available from GSI Lumonics, Watertown, Mass.), or an acousto-optic scanner (available from Electro-Optical Products Corp., Fresh Meadows, N.Y.) to scan the beam from point A to B (the X direction). A pair of XY galvanometric scanners or acousto-optic scanners may be used to scan the beam in two dimensions. An alternative is to use the design of FIG. 32 to scan in the X direction (from A to B) and a mechanical stage to scan in the Y direction (in and out of the page). This design uses an S polarized laser diode 3201 that is directed onto a scanner 3202 that scans the beam 3209 in a clockwise motion. The scanner is placed at the back focal plane of the scan lens 3206. That is, the scanner (in this case a rotating polygon) 3202 is placed one focal length along the beam path from the scan lens 3206. The scanned beam is incident upon a polarizing beam splitter 3204 and totally reflects onto quarter wave plate 3205 and then a scan lens 3206 where it is scanned from points A to B. Upon reflecting from the substrate 3208 at points A or B the beams pass through a second scan lens 3206 and are incident upon a retro-reflector 3207 placed at the back focal plane of the scan lens 3206. The retro-reflector causes the beams to retrace their path and upon passing a second time through the quarter wave plate 3205 the beam becomes P polarized and passes through the polarizing beam splitter 3204 and is incident upon a quadrant detector 3203 which is placed at a point near the back focal plane of the scan lens 3206. The beam is scanned across the quadrant detector 3203 in the direction shown.

In order to separate slope and height terms according to one embodiment of the present invention a mirror image the design is used at the top of FIG. 32 and this is shown at the bottom of FIG. 32 as 3210. This embodiment 3210 can also have its polygon scanner rotating in a clockwise direction so that both beams will scan from points A to B. When the outputs from the quadrant detectors of the designs at the top and bottom of FIG. 32 are added together then the resulting signal will give a signal which is proportional to the height of the substrate 3208 and independent of its slope. That is, the slope terms will cancel and the height terms will add. The signal will also be independent of the reflectivity of the material for the reasons discussed in earlier paragraphs. One aspect of the design of FIG. 32 is seen in the large difference in path lengths of the beams that are directed at points A and B. This means that in order for the beam to remain in focus over this large path length difference this design is best utilized at low resolution, since a large depth of focus (large spot size) design must be used.

Figure 33:
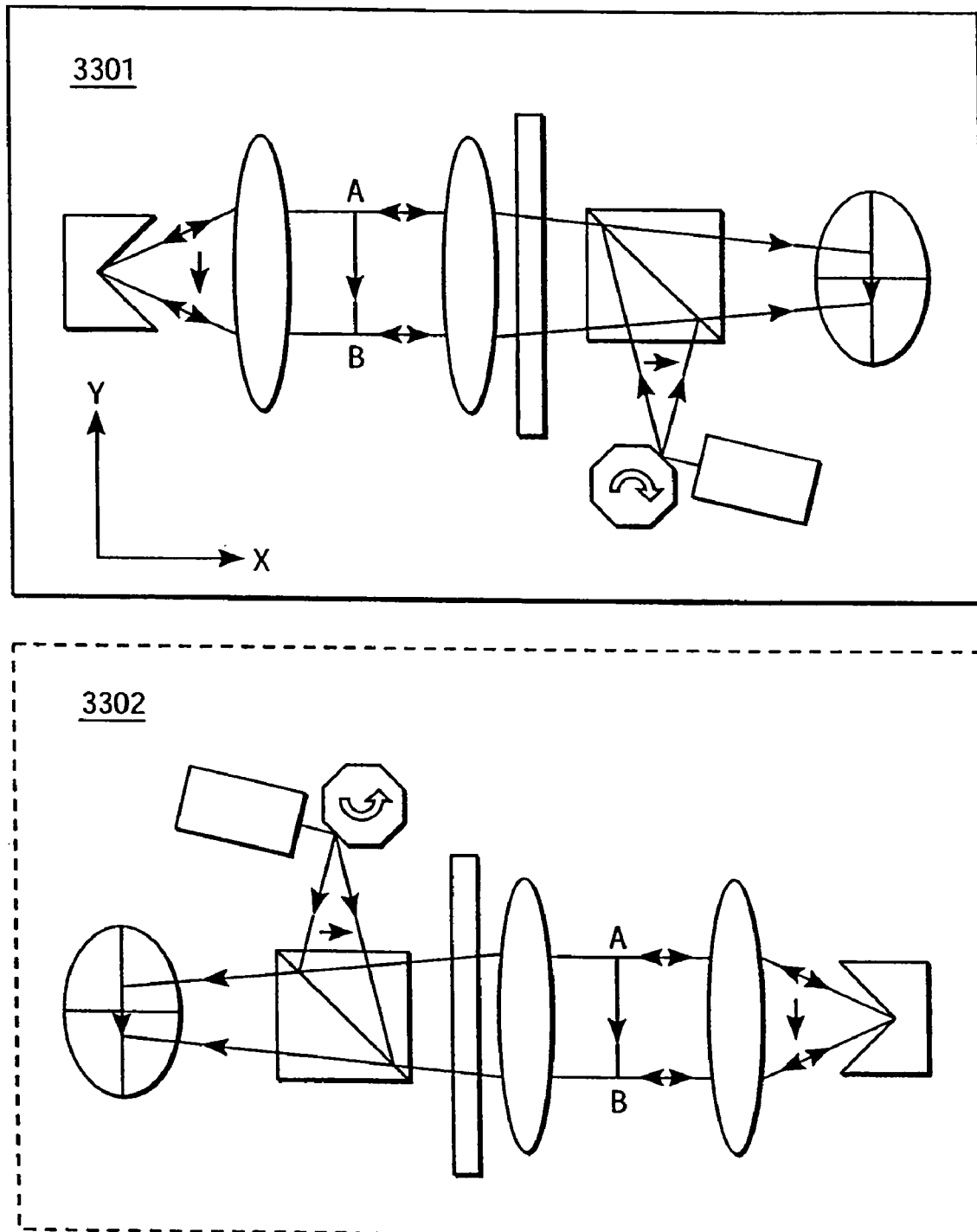
FIG. 33 is an illustration having a top view perspective of an optically scanned material independent optical profilometer according to another embodiment of the present invention.

An alternate embodiment that increases the resolution is shown in FIG. 33 as 3301. In this design the laser diode 3201, polygon scanner 3202, and polarizing beam splitter 3204 of FIG. 32 are rotated by 90° so that the laser and polygon are now arranged as shown in FIG. 33, 3301. All the other components remain unchanged. The view of FIG. 33 is from the top of device whereas that of FIG. 32 is from the side. The embodiment of 3301 scans the beam from points A to B and since the path lengths from the scan lens to A and B are equal then a much higher (smaller spot size) resolution optical design may be used. In order to separate slope and height according to one embodiment of the present invention, a mirror image 3301 about the line AB is used to create a second head (analogous to FIG. 32) as shown as 3302 whose quadrant detector output is added to the quadrant detector of 3301. This will separate slope and height in the same manner as FIG. 32. As shown in FIG. 33 the polygon scanner moves the beam in the Y direction. A mechanical stage (not shown) or a second polygon scanner may accomplish the X direction scan.

Figure 36:
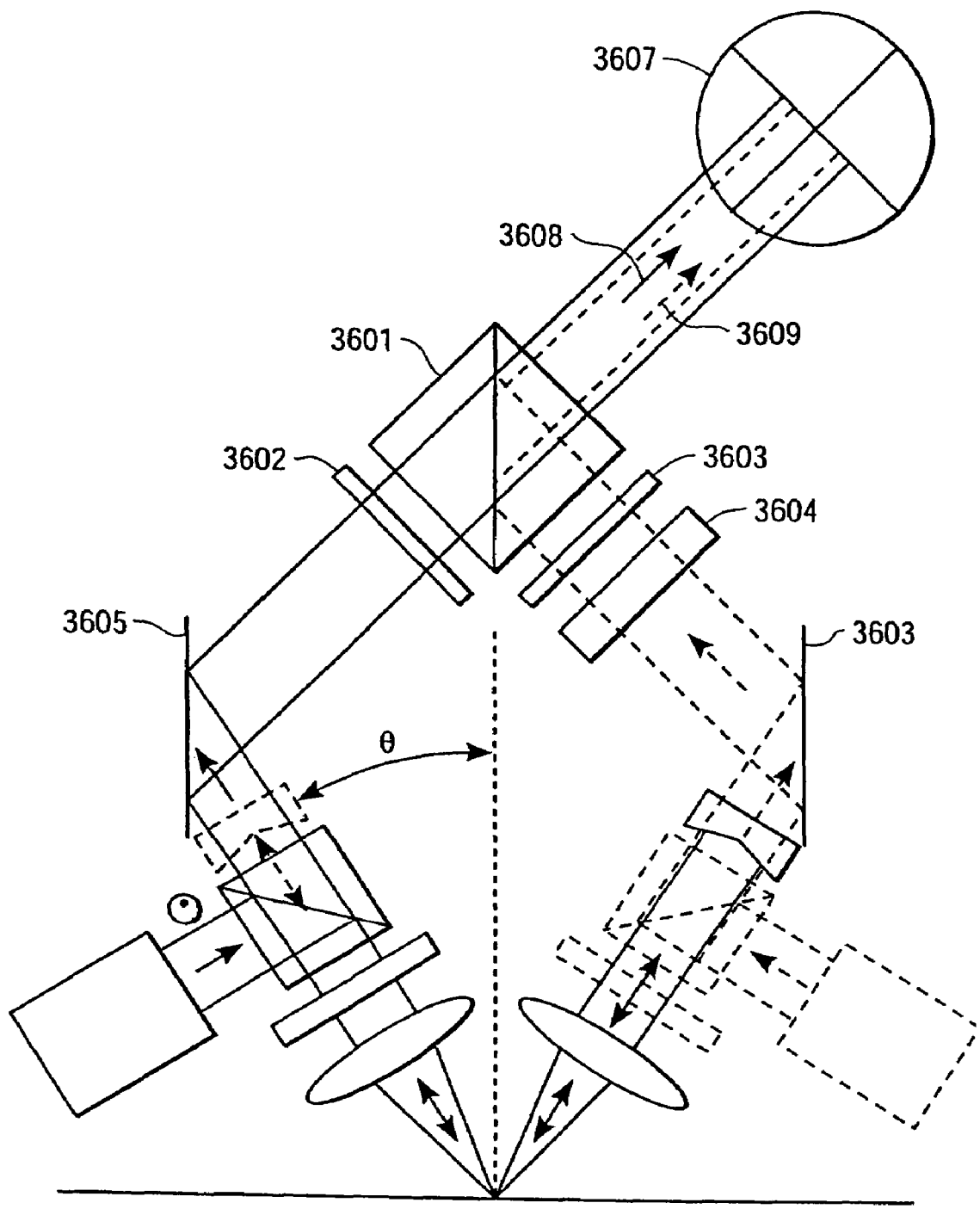
FIG. 36 is an illustration of a material independent optical profilometer having one detector according to one embodiment of the present invention.
Figure 37:
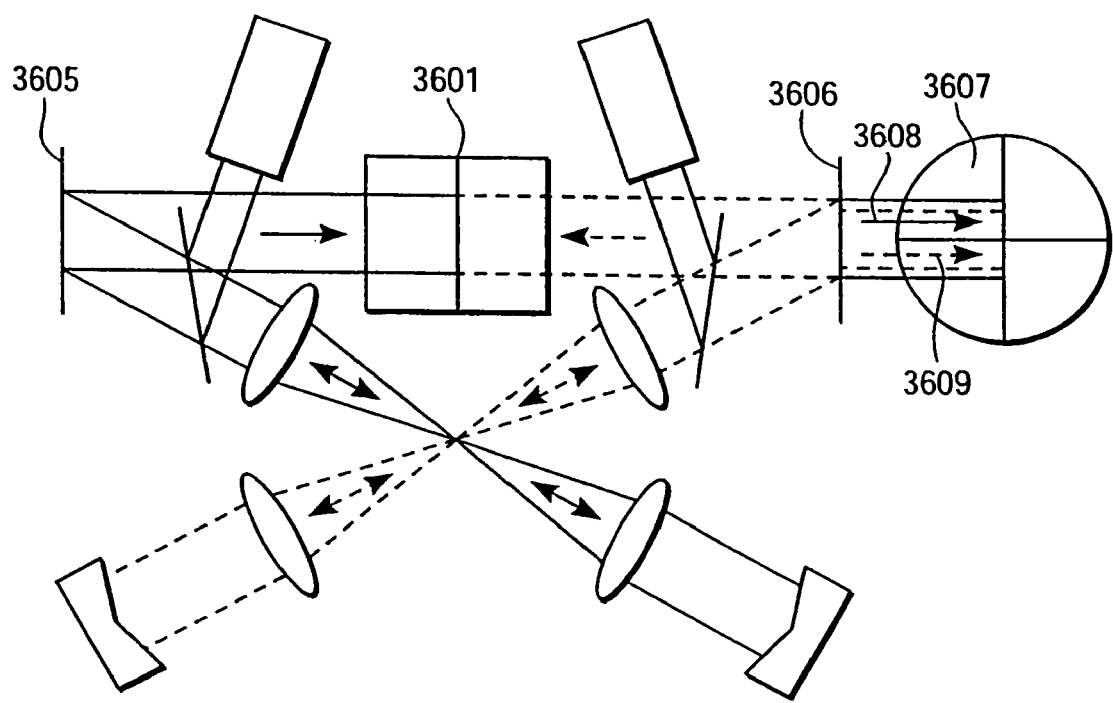
FIG. 37 is an illustration from a top view perspective of a material independent optical profilometer having one detector according to one embodiment of the present invention.

FIG. 36 shows a side view of another embodiment of a material independent optical profilometer that uses a single detector. This design is similar to that shown in FIGS. 19, 20, 21, 22, 23, 24, and 25 except that only a single detector is required in FIG. 36. 3601 is a conventional polarizing beam splitter, 3602 is a linear polarizer oriented in the P orientation, 3603 is a linear polarizer oriented in the S orientation, 3604 is a 90° polarization rotator, which may be a half wave plate or optically active quartz, 3605 and 3606 are turning mirrors, 3607 is a quadrant detector, 3608 is the beam from one half of the mirror imaged optical system and 3609 is the beam from the other half of the optical system. The two halves of the mirror imaged optical system are shown as the solid and dashed lines in FIG. 36. The solid and dashed halves of the optical system are not in the same plane as shown in FIG. 37. The advantage of the design of FIGS. 36 and 37 is that it uses only a single detector which eliminates the issue of achieving identical (or substantially identical) detectors as used in the designs of FIGS. 19 through 25. FIG. 37 shows the design of FIG. 36 as seen from the top with the components labeled as in FIG. 36. The dashed beam in FIG. 37 corresponds to the dashed beam in FIG. 36. Note that the beams that strike the detector 3607 are orthogonally polarized and as a result will not interfere. The signal from the two beams 3608 and 3609 are optically added when they strike the detector 3607. As a result the signal output from 3607 will be proportional to the height of the object imaged and independent of its reflectivity or slope.

The quadrant detectors shown in FIGS. 3-6, 8-10, 12, 15, 19-33, 36 and 37 may be replaced by conventional position sensitive detectors such as model S5991 available from Hamamatsu Photonics K.K., Hamamatsu City, Japan or by bi-cell detectors also available from Hamamatsu.

The detection of the optical signal is done over a bandwidth from DC to 3 MHz since this is the bandwidth of the quadrant detectors as described in the preceding text. This bandwidth may be filtered as appropriate to remove mechanical vibration, optical noise, or stray light signals. An alternate detection scheme is to modulate the laser intensity and to synchronously detect the signal from the quadrant detectors at the laser modulation frequency. This method will greatly improve the signal to noise of the detected signal and will reject external noise sources such as vibration. The disadvantage of this approach is that the speed of data acquisition will be greatly reduced.

Figure 38:
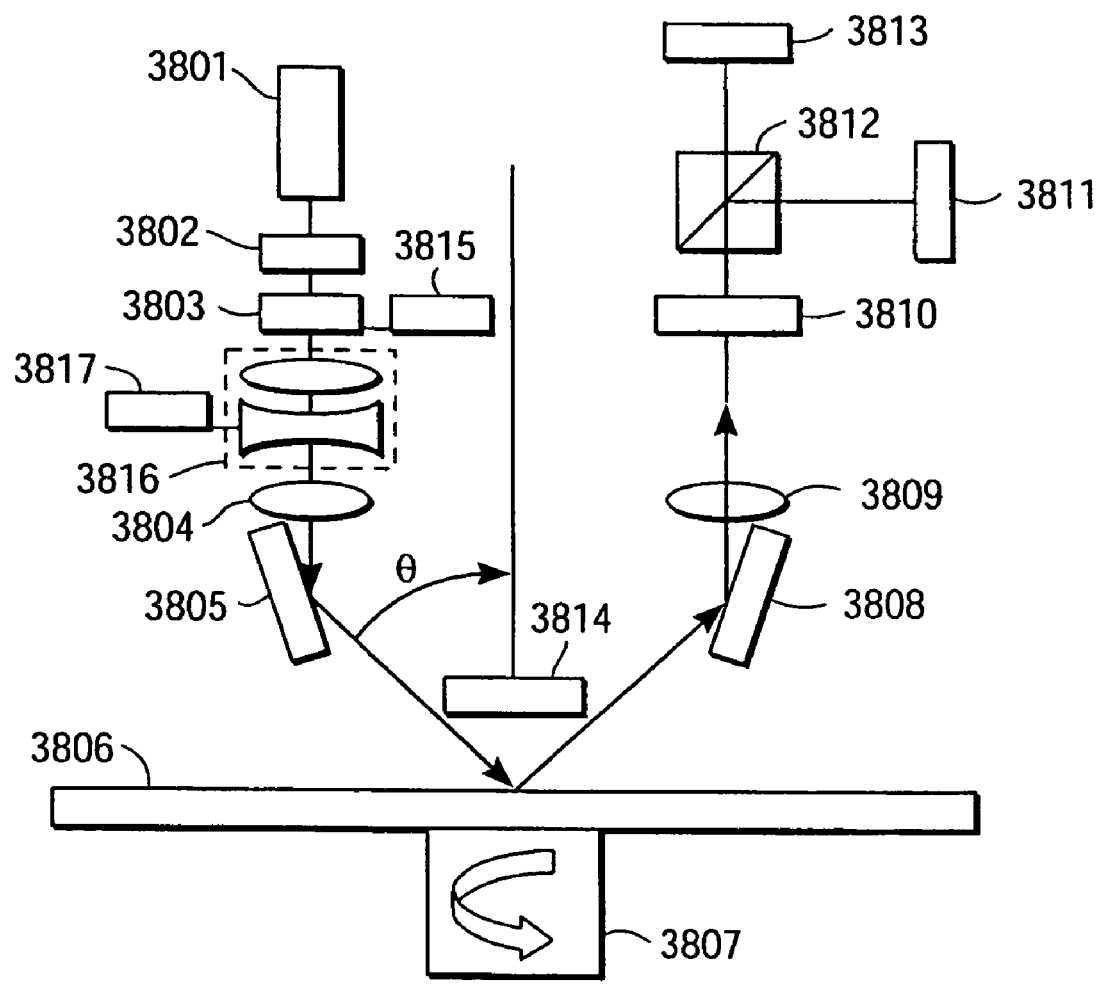
FIG. 38 is an illustration of an optical profilometer, ellipsometer, reflectometer and scatterometer which uses a telescope to produce user selectable multiple spots sizes on a substrate.

A multiple spot size optical surface analyzer is shown in FIG. 38 according to one embodiment of the present invention. The optical surface analyzer includes a laser diode with internal feedback photodiode 3801, a linear polarizer 3802, a half wave plate 3803 with a motor 3815 for rotating the half wave plate so that P, S and 45. degree. polarization is available. The optical surface analyzer also includes a Galilean or Keplerian telescope 3816 for expanding or diminishing the beam diameter. This telescope 3816 may be moved in and out of the beam via a motor 3817.

Multiple beam diameters may be achieved by moving different magnification Galilean or Keplerian telescopes into the beam via the motor 3817. The embodiment of FIG. 38 shows only two possible beam diameters (the original beam diameter and the expanded one with 3816 present in the beam), however any number of beam diameters may be achieved by using a series of different magnification Galilean or Keplerian telescopes attached to the motor 3817. An alternative embodiment can use a continuously variable magnification telescope such as model K61-386 available from Edmund Industrial Optics, Barrington, N.J., USA. If this type of telescope is used to replace 3816 then a continuous range of beam diameters and hence focussed spot sizes is possible. The motor 3817 can be computer controlled to adjust the continuously variable magnification telescope 3816 to give the desired beam diameter and hence spot size.

The different beam diameter will change the focussed spot size on the substrate 3806 in direct proportion to the magnification or diminution produced by the telescope 3816. With reference to FIG. 38, the system includes a focussing lens 3804, a turning mirror 3805, the substrate 3806, a spindle motor 3807, a turning mirror 3808, a collimating lens 3809, a quarter wave plate 3810, a quadrant detector 3811, a polarizing beam splitter 3812 rotated at 45. degree. to the plane of incidence, a quadrant detector 3813, and a scattered light detector 3814 which may be a PMT tube, a PIN photodiode or an avalanche photodiode.

Some of the advantages of this design are that multiple focussed spot sizes are available in a single optical system and the system does not need to be refocussed when a different beam diameter is selected. This is because the beam diameter is selected before the beam is focussed and the incoming beam is always collimated regardless of magnification. The advantage of multiple spot sizes is that smaller spot sizes generally give better sensitivity and resolution but slower throughput. A system which has multiple spot sizes can be automatically configured to the desired sensitivity and throughput by a simple choice of spot size. The motor 3817 is controlled by a connection to a small computer so that the beam diameter (and hence spot size) may be selected by commands given to the computer. The multiple spot size idea may be applied to the multiple beam designs described in FIGS. 16, 19, 20, 21, 22, 23, 24, 25, 26, 27, 28, 29, 30, 31, 32, 33, 34, 36, and 37.

Figure 39:
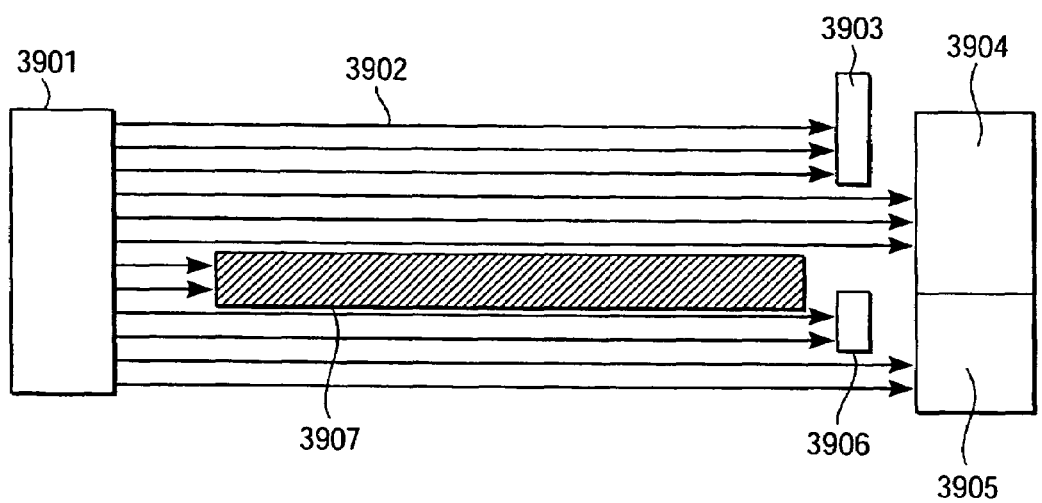
FIG. 39 is an illustration of a method of detecting the thickness of a disk or wafer.

Another problem in the inspection of disk drive media and wafers is determination of the thickness of different drive media and wafers. FIG. 39 shows an embodiment of a system and method for measuring the thickness of thin film disks, wafers, substrate, or other substantially planar objects. In this embodiment, laser diode 3901 transmits a beam 3902 towards a bi-cell 3904 and 3905 or a quad-cell or a pair of separate photodiodes or another position sensitive detector. In another embodiment, the light beam source for beam 3902 may be a collimated light source. In the embodiment depicted in FIG. 39, beam 3902 is directed substantially parallel to the surface of the disk or wafer and positioned so that the disk or wafer 3907 is at the center of the beam 3902. In other embodiments, other positions of beam 3902 relative to the disk or wafer may be selected so long as portions of the beam pass both above and below the wafer or disk. The amount of light beam intensity received at top detector 3904 depends on the thickness of the disk. As the disk thickness increases, more of the laser beam is blocked by the disk or wafer 3907 resulting in a decrease in the amount of laser beam intensity reaching top detector 3904. In response to the impinging light beam intensity, the detector generates a signal proportional to the amount of light beam intensity received at the top detector. Thickness mask 3903 blocks unecessary light from the laser to aviod saturating the top detector and to increase the sensitivity of the system to changes in thickness. The reference mask 3906 is positioned such that the bottom detector 3905 receives the same amount of light beam intensity regardless of the disk thickness. The reading from the bottom detector 3905 is used to normalize for any drift in the laser power, electronics or receiving optics.

Figure 40:
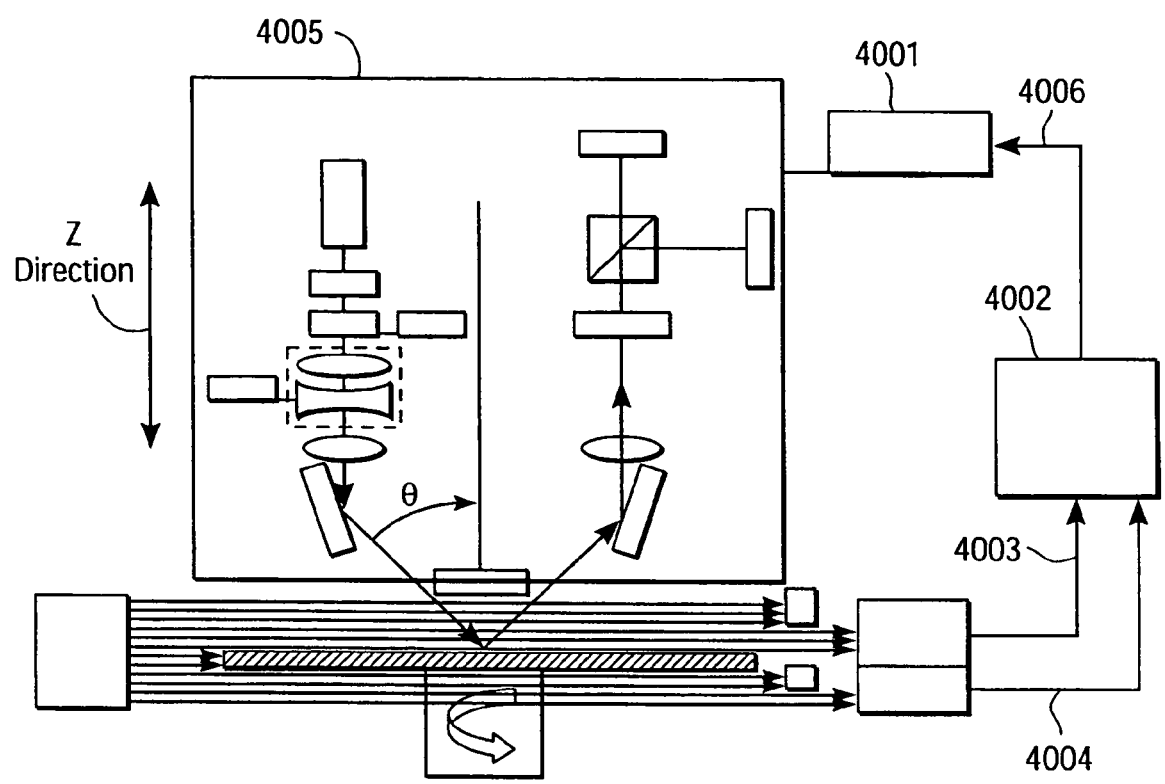
FIG. 40 is an illustration of a thickness detector integrated with an optical surface analyzer.

FIG. 40 shows the thickness detector integrated with an optical surface analyzer 4005. The signal from the thickness detector is fed back via lines 4003 and 4004 to a processing device 4002. Any of a variety of processing devices 4002 can be used, such as a microprocessor or a personal computer. In one embodiment, the processing device 4002 analyzes the data and determines the disk or wafer thickness from the data. The processing device 4002 then commands a motor 4001 (via line 4006) which is attached to the optical surface analyzer 4005. The motor 4001 raises or lowers the optical surface analyzer 4005 in the Z direction so as to compensate for any increase or decrease in the disk or wafer thickness as measured by the thickness detector. In this manner the optical surface analyzer 4005 will automatically remain in focus during optical surface analysis of substrates with different thicknesses. This invention also prevents the optical head 4005 from inadvertently crashing into a thick disk or wafer since the distance from the optical head to the wafer is automatically maintained at a fixed distance. The shadow technique used in this invention is effective for measuring the thickness of both opaque and transparent disks or wafers.

As the technology for the semiconductor and the disk drive industries continues to advance there is a need to detect and classify ever smaller defects. Examples of such defects include scratches, pits and particles. When scratches have a length greater than the dimension of the laser spot projected on the surface of the object, it is possible to classify the scratch based upon its detected aspect ratio (its shape). That is, the scratch is longer than it is wide. When a scratch is smaller than the dimension of the laser spot this type of classification is not possible. As a result, in conventional systems it is not possible to classify a small scratch as different from a particle. The present invention presents a technique to detect and classify scratches, pits, particles, and other defects which are smaller than the laser beam spot size.

Figure 41:
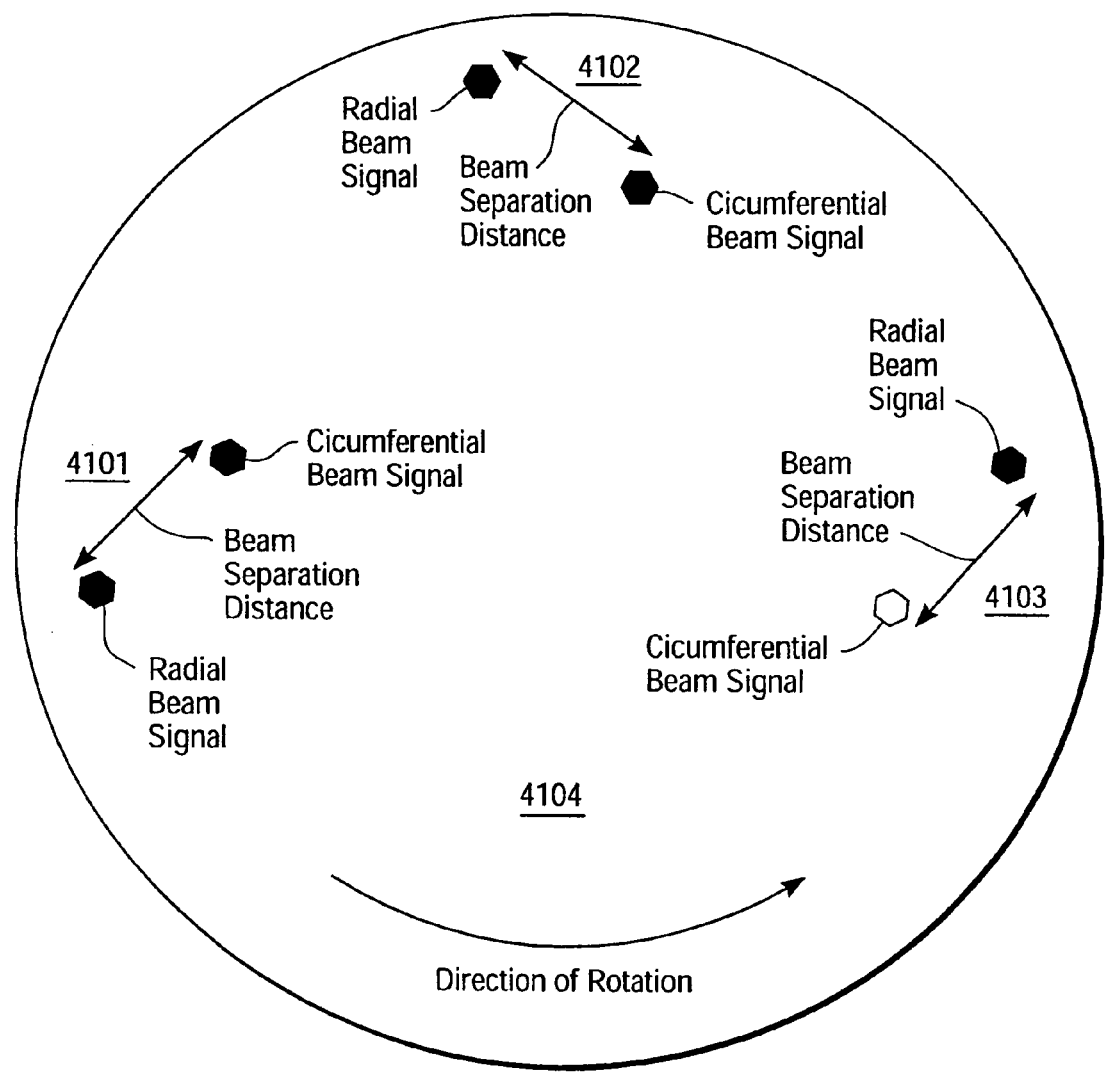
FIG. 41 is an illustration of the scattered light detection of a particle, pit, and scratch using two orthogonal beams.
Figure 42:
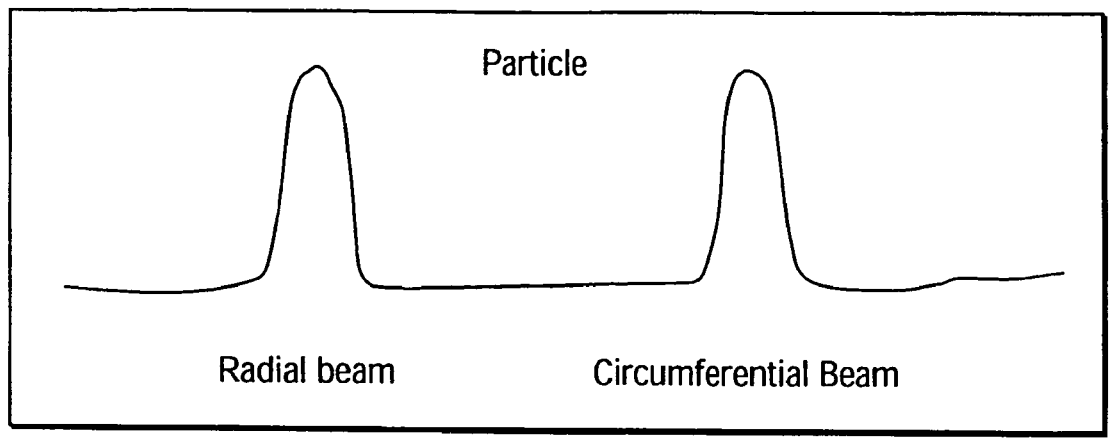
FIG. 42 is an illustration of the scattered light signals for a particle, pit and a scratch from both the radial and circumferential beams.
Figure 42:
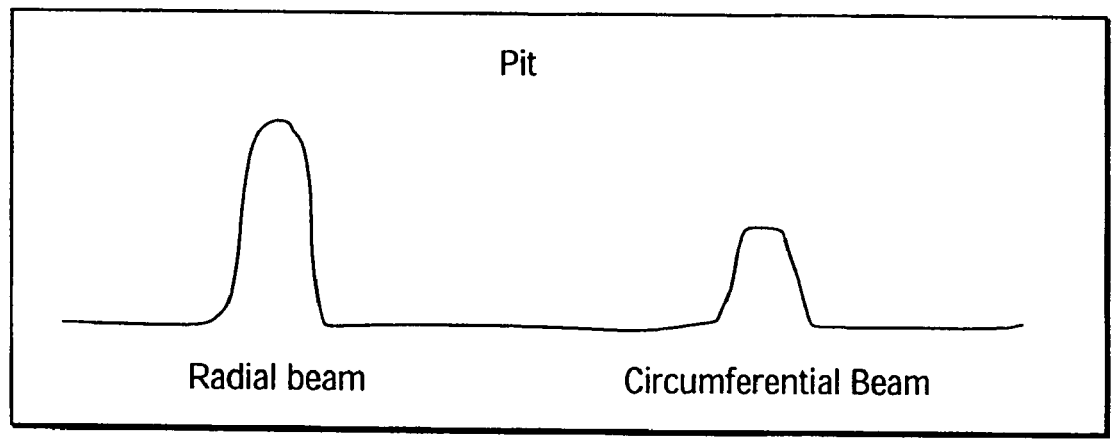
Figure 42:
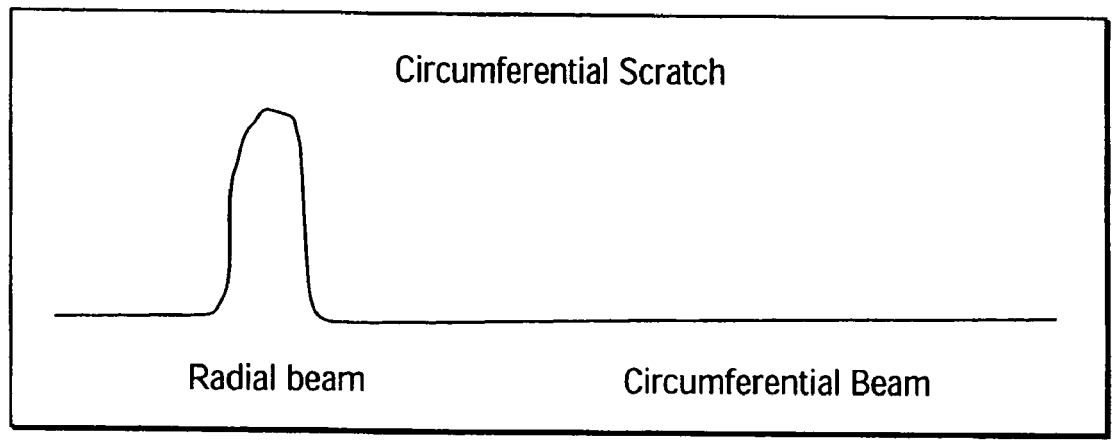

The optical device shown in FIG. 38 can be arranged so that there are two identical sets of optics with orthogonal planes of incidence. In an embodiment, the plane of incidence of laser beam one is in the circumferential direction and the plane of incidence of laser beam two is in the radial direction as shown in FIGS. 4 and 16. The scattered detector 314 (on FIG. 3) and 3814 (on FIG. 38) will receive scattered light from both beams as the optical device is moved over the surface of the spinning wafer or disk. Scratches which are oriented perpendicular teehe plane of incidence of the light will generate a strong scatter signal, while those oriented parallel to the plane of incidence will generate substantially no scattered~signal. For example, a circumferentially oriented scratch will generate a strong scatter signal when the radial beam (laser 2 in FIG. 4) crosses it and substantially no scatter when the circumferential beam (laser 1 in FIG. 4) crosses it. By contrast, a particle which is substantially isotropic in shape will generate scatter from both the radial and circumferential laser beams. This is illustrated in FIG. 41 where a dual beam system consisting of two set of the optics shown in FIG. 38 are arranged with one laser beam in the radial plane of incidence and one in the circumferential plane of incidence of the wafer or disk 4104 shown in FIG. 41. This laser orientation is also illustrated in FIGS. 4 and 16. The radial plane of incidence beam is displaced from the circumferential plane of incidence beam in such a way that the wafer or disk encounters it first. The radial and circumferential plane of incidence beams are also displaced slightly in the circumferential (angular) direction as shown in FIG. 41. The distance between the beams is fixed and constant. Since a small particle is substantially isotropic it will scatter substantially equally when illuminated by the radial or circumferential beam as shown by the two black hexagons in 4101. The black hexagon of 4101 closest to the OD of the wafer or disk is the signal received by detector 3814 resulting from the radial beam illuminating the particle. The black hexagon of 4101 nearer the ID of the wafer or disk is that resulting from the circumferential beam illuminating the particle. In the case of a substantially isotropic particle the signals from both black hexagons of 4101 are substantially equal. The case of a circumferentially oriented scratch is shown in 4103 where the radial beam gives a strong signal and the circumferential beam gives substantially no signal. This is because the scratch is strongly anisotropic in its scattering characteristics. That is, a beam whose plane of incidence is oriented perpendicular to the long direction of the scratch scatters much more than a beam whose plane of incidence is parallel to the long direction of the scratch. The scattering from a scratch is also polarization dependent. At an angle of incidence of approximately 60. degree. a P linear polarized radial beam will produce the largest scattered signal from a circumferentially oriented scratch. P linear is the preferred polarization but S polarization, 45. degree. linear polarization, circular or elliptical polarization will also give acceptable signals. In 4103 the radial beam gives a strong scattered signal from the scratch and if one looks for a signal at the beam separation distance corresponding to the circumferential beam one finds substantially no signal for this circumferential scratch. Here, the beam separation distance refers to the time required for an object location to travel from the position of the first beam to the position of the second beam. The length of this offset time between the two signals will be dependent on the offset distance between the beams and the rotational speed of the wafer. The case for a small oval shaped pit whose major axis is along the circumferential direction is shown in 4102. In this case the radial beam give a strong signal as shown by the black hexagon in 4102 and the circumferential beam give a small signal as shown by the gray hexagon. The ratio of the scattered amplitudes of the black and gray hexagons will discriminate the pit from a scratch or particle. This is illustrated in FIG. 42 which shows at the top the relative amplitudes of the scattered light of the particle in the radial and circumferential beams. In this case the amplitudes are substantially equal. The middle picture in FIG. 42 shows the amplitudes for a small oval shaped pit. The amplitudes are not equal. The bottom picture in FIG. 42 shows the amplitudes for a circumferentially oriented scratch. In this case the scatter signal comes substantially only from the radial beam. If the scratch were oriented in the radial direction the scatter signal would come substantially from the circumferential beam and substantially none from the radial beam. If the scratch were oriented at 45° to the radial direction then the scattered signal would be equal from both the radial and circumferential beams. It is also possible to orient the planes of the laser beams at angles other than 90°. In another embodiment, the orthogonal pair of beams may be oriented at an angle to the radial and circumferential directions. In this manner one may more easily detect scratches which lie at directions which are neither radial nor circumferential.

In an embodiment, the apparatus to detect scratches and particles is that shown in FIG. 38 except that there are two identical heads arranged with their planes of incidence at 90 degrees. This optical head moved over the rotating disk and a scattered light image is collected from each radius and angle on the disk surface. This data is processed by denoting excursions (above or below) of the data from the local average. The local average is determined by averaging the data for a specified length along a specified orientation such as the radial or circumferential direction. The local average is moved throughout the entire data set and each pixel is compared to the local average. Points, which exceed the specified threshold above or below the local average, are denoted as defects. All the points, which exceed the specified threshold, are put together in a map of the surface showing the locations and amplitude of all the defects. Contiguous or substantially contiguous points on the defect map are classified as a single defect. The amplitude of the scattered light from the radial and the circumferential beams are then compared to determine if the defect is a scratch, particle or pit.

In an embodiment of the above-described functions and features for comparing and classifying defects, a computing device with a central processing unit (CPU) is used to process the scattered lighter image data collected from the disk surface. The CPU executes the above-described algorithm to process the images in order to compare and classify the defects. For example, the algorithm can be implemented as a computer program stored on a conventional storage device, in firmware or in hardware.

Note that in the case where a scratch (which is smaller than the beam size) or other defect is oriented at 45° to the radial direction, a system involving two orthogonally oriented beams will not be able to distinguish a particle from a pit or scratch. More generally, when the long axis of an anisotropic defect bisects the angle formed by the planes of incidence between the two incident beams, the resulting scattered signals will not readily distinguish particles from anisotropic defects such as, scratches. In these situations, the true nature of the defect may be determined by generating a third scattered signal and a fourth scattered signal. In an embodiment, these scattered signals should be generated by incident beams that lie in planes which are at 45° relative to the planes of the first two incident beams. More generally, the third and fourth scattered signals should be generated by incident beams which lie in planes distinct from the planes of the first and second incident beams. In another embodiment, the third and fourth beams may be generated by a third and fourth laser or other beam source. In yet another embodiment, the third and fourth beams may be generated by changing the plane of incidence of both sets of optics. Another possible embodiment is to continuously rotate the plane of incidence of the orthogonal beams while scanning the disk or wafer. In this manner all possible planes of incidence may be incident upon the wafer or disk. Other possible embodiments will be apparent to those skilled in the art.

The scatter detector 3814 in FIG. 38 may have a condenser lens in front of it to increase the cone of scatter angles that it may receive. An alternative embodiment is to place the scatter detector 3814 on top of a hole in an integrating sphere. The two laser beams pass through the integrating sphere and all the scattered light angles are gathered by the integrating sphere and measured by the detector 3814 at the top of the sphere. The detector 3814 may be a silicon or germanium photodiode, an avalanche photodiode or a photo multiplier tube.

The advantages of this technique are improved sensitivity to scratches, pits and particles, (which may be smaller than the beam spot size), improved ability to identify (classify) scratches, pits, and particles, and no blind spot to scratches, (as would be the case of a circumferential beam and a circumferential scratch).

Figure 43:
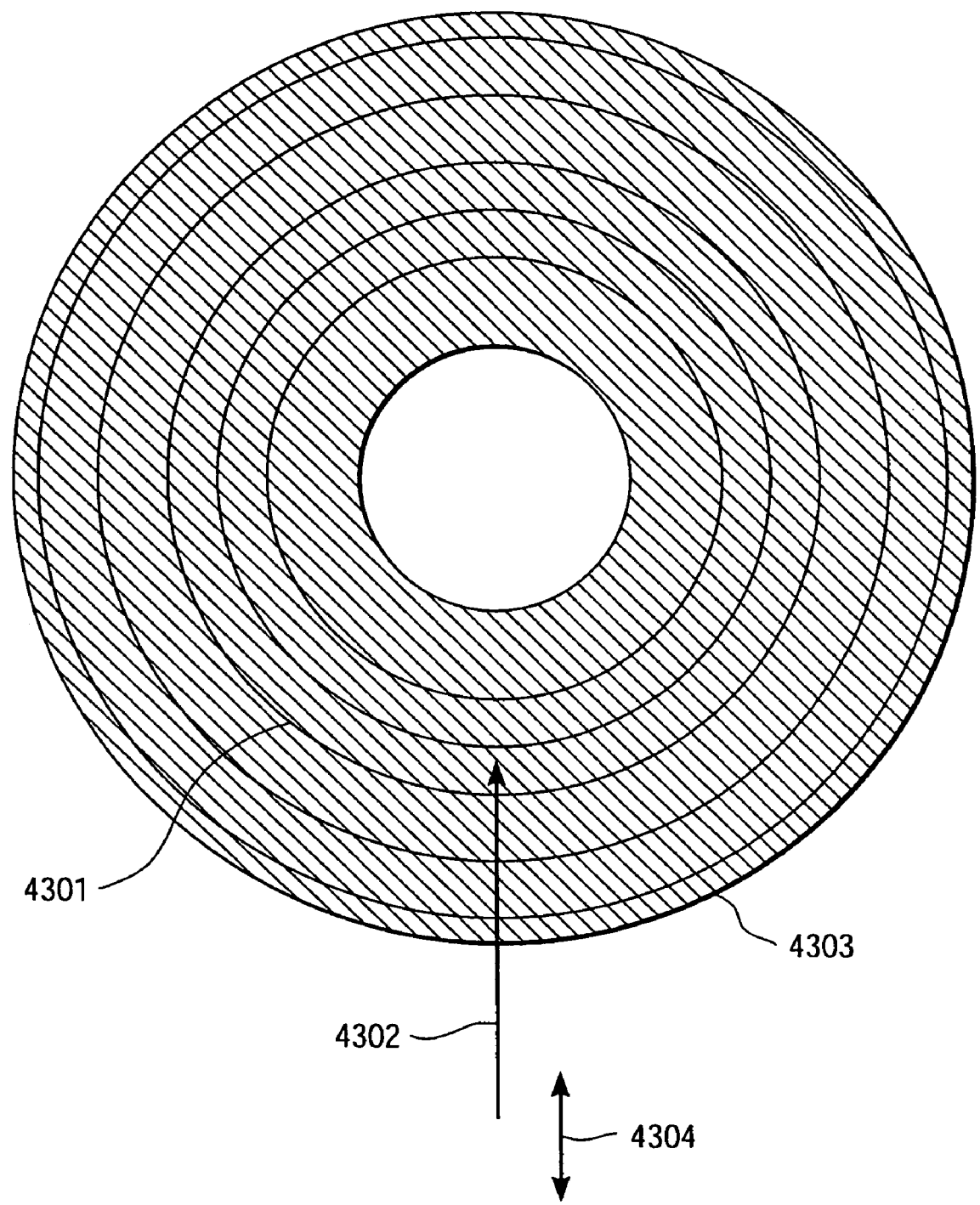
FIG. 43 is an illustration of a detection surface with arrows to show the orientation of an optical head with a radially oriented laser beam for detecting circumferential texture scratches.

The previous embodiments have described optical designs that compare a radial and a circumferentially oriented optical head to determine if a defect is a scratch or a particle. It is also possible to detect and classify a defect as a scratch or a particle by using only a single optical head. The case of detecting circumferential scratches is shown in FIG. 43. This is accomplished by orienting the plane of incidence of the optical head shown in FIG. 38 in the radial direction as indicated by 4302. The optical head 4302 is attached to a mechanical linear stage and moved in the radial direction as indicated by 4304. In this manner, the circumferential texture scratches 4301 on disk or wafer 4303 will have the maximum amount of scattered light. The amount of scatter from the circumferential texture is typically so great that only large particles may be detected. As a result, much of the information detected by the embodiment described by FIG. 43 is from the circumferential texture. The texture defects are noted by excursions in scattered amplitude that are significantly above the background. The texture defects are separated from the signal for large particles by using an algorithm that measures the aspect ratio of the detected defect. A texture scratch will have a long and thin aspect ratio and a large particle will not.

In an embodiment, the apparatus to detect circumferential scratches and particles is that shown in FIG. 38 with the optical plane of incidence oriented in the radial direction. The optical head of FIG. 38 is moved over the rotating disk and a scattered light image is collected from each radius and angle on the disk surface. This data is processed by denoting excursions (above or below) of the data from the local average. The local average is determined by averaging the data for a specified length along a specified orientation such as the radial or circumferential direction. The local average is moved throughout the entire data set and each pixel is compared to the local average. Points, which exceed the specified threshold above or below the local average, are denoted as defects. All the points, which exceed the specified threshold, are put together in a map of the surface showing the locations and amplitudes of all the defects. Contiguous points on the defect map are classified as a single defect. The aspect ratio (length to width ratio) is tested for each unique defect consisting of contiguous points. If the aspect ratio is long and thin then it is classified as a circumferential scratch, if not then a particle. The same process may be applied to the data from a circumferentially oriented head, but in this case, a long aspect ratio means a radial scratch and a short ratio a particle.

In an embodiment of the above-described functions and features for comparing and classifying defects, a computing device with a central processing unit (CPU) is used to process the scattered lighter image data collected from the disk surface. The CPU executes the above-described algorithm to process the images in order to compare and classify the defects. For example, the algorithm can be implemented as a computer program stored on a conventional storage device, in firmware or in hardware.

Figure 44:
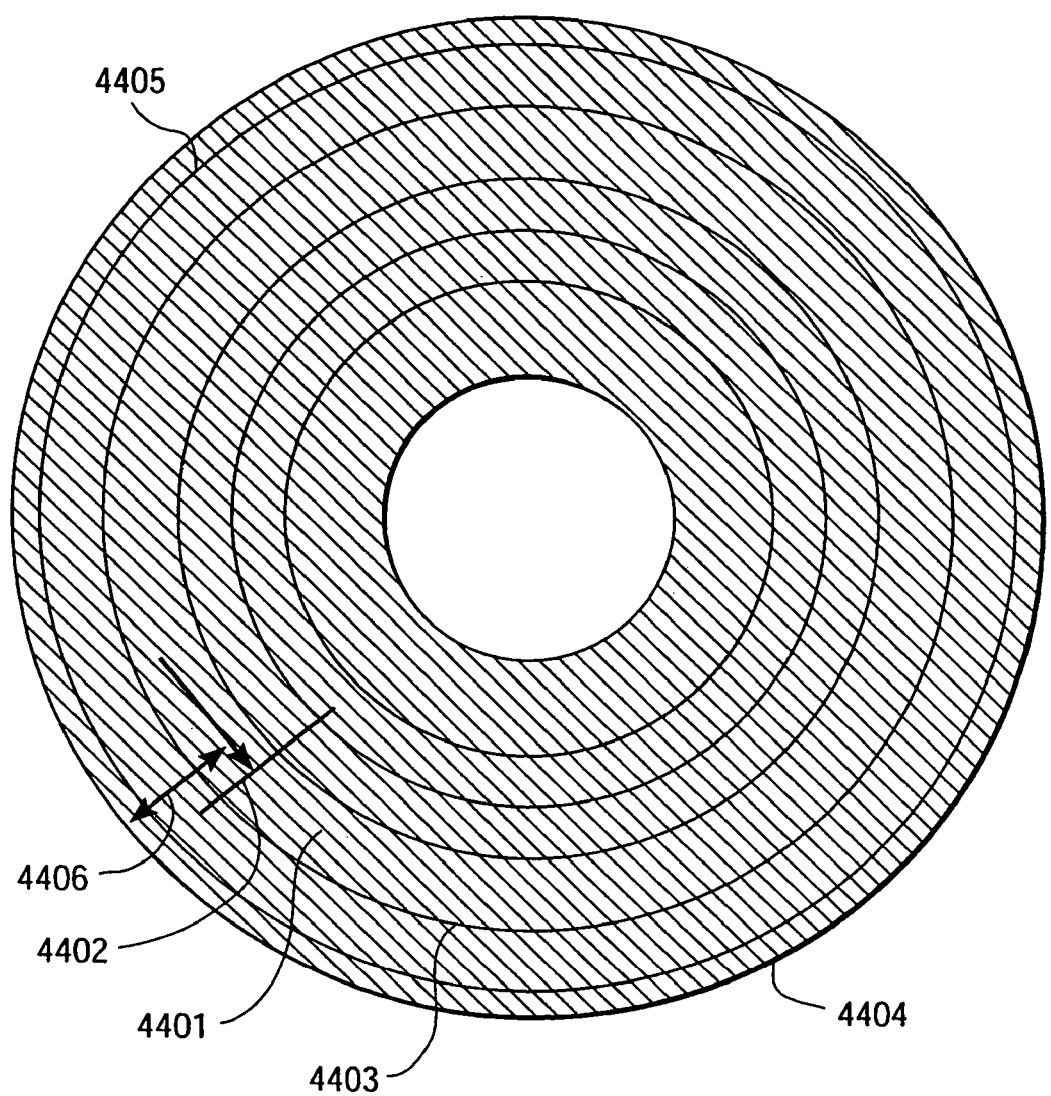
FIG. 44 is an illustration of a detection surface with arrows to show the orientation of an optical head with a circumferentially oriented laser beam for detecting radial scratches and particles.

The case of detecting radial scratches or particles is shown in the embodiment shown in FIG. 44. In this case, the optical head in FIG. 38 is oriented above the disk or wafer 4404 in the circumferential direction 4405 and optimal scatter will come from radial scratches 4402 and particles 4401. The optical head 4405 is attached to a mechanical linear stage and moved in the radial direction as indicated by 4406. The circumferential texture 4403 will not scatter in this embodiment. The advantage of this design is that it allows optimal measurement of particles and radial scratches since the circumferential texture does not scatter light and hence does not add to the background "noise".

Figure 45:
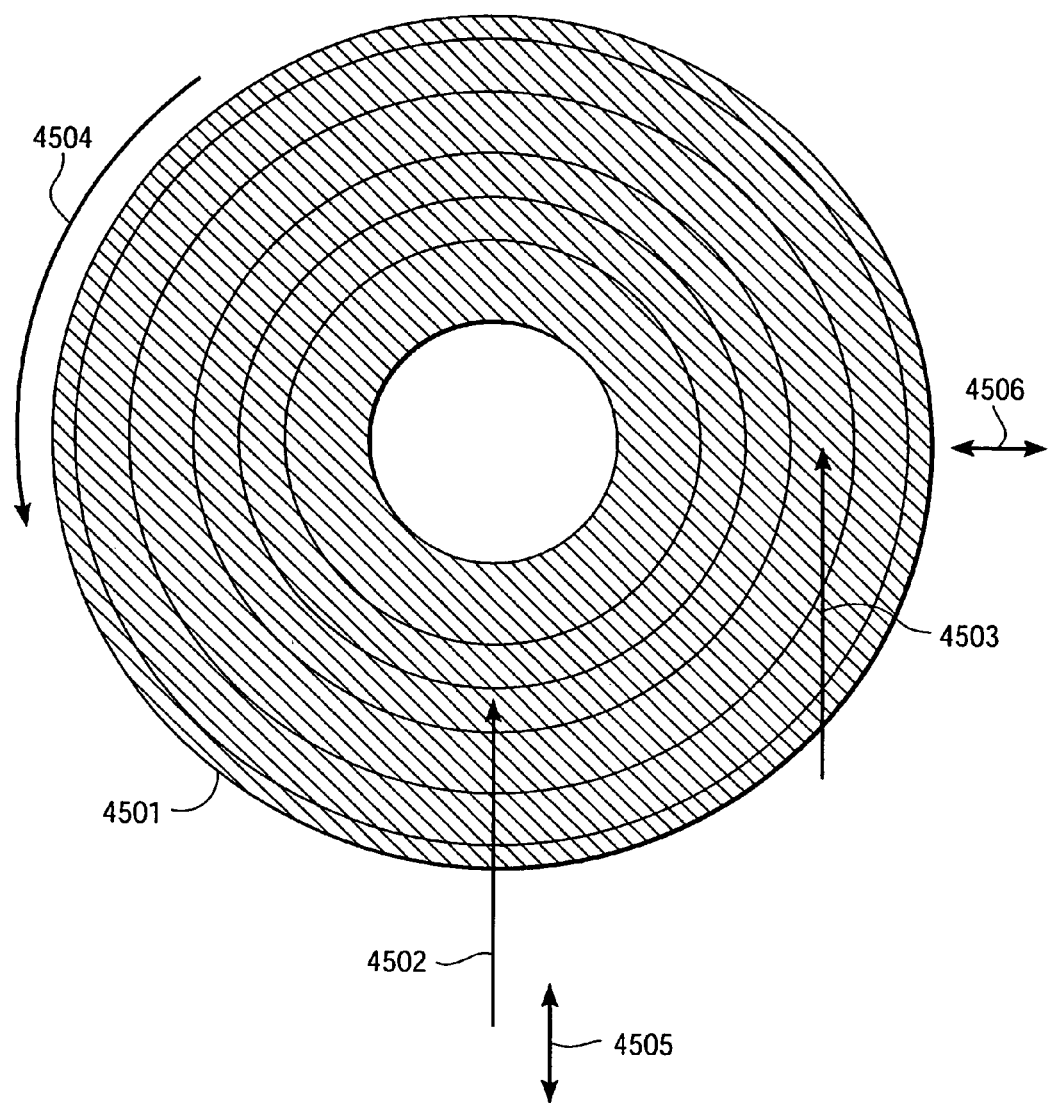
FIG. 45 is an illustration of a means of detecting scratches and particles with two optical heads whose optical planes of incidence are parallel but whose scanning directions are separated by 90 degrees.

Previous embodiments discussed the detection of radial and circumferential scratches and particles using two optical heads (like those of FIG. 38) with orthogonally oriented planes of incidence. The embodiment shown in FIG. 45 shows how this may be accomplished with two optical heads like those of FIG. 38 whose laser beams have the same plane of incidence. The laser beams of optical heads 4502 and 4503 may come from the same laser or from two different lasers. The laser in optical head 4502 is oriented in the radial direction and is mounted on a mechanical linear stage 4505 that moves in the radial direction as indicated in FIG. 45. The disk or wafer 4501 is rotated in the clockwise or counter-clockwise direction 4504. The laser in optical head 4503 is oriented in the circumferential direction and is mounted to a mechanical linear stage 4506 which is oriented at an angle of 90 degrees to stage 4505. Stage 4506 also moves in the radial direction but at a position which is 90 degrees from stage 4505, as indicated in FIG. 45. In this manner, circumferential texture scratches may be detected by optical head optical head 4502, and particles and radial scratches may be detected by optical head 4503. The advantage of this design is that both optical heads may be scanned at the same time and information on circumferential and radial scratches and particles may be detected simultaneously.

While the invention has been particularly shown and described with reference to a preferred embodiment and various alternate embodiments, it will be understood by persons skilled in the relevant art that various changes in form and details can be made therein without departing from the spirit and scope of the invention. While the invention has been particularly shown and described with reference to a preferred embodiment and various alternate embodiments, it will be understood by persons skilled in the relevant art that various changes in form and details can be made therein without departing from the spirit and scope of the invention.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system for measuring a height of an object comprising:
    a first electromagnetic signal source for transmitting a first signal toward a first position on the object at a first angle;
    a second electromagnetic signal source for transmitting a second signal toward the first position on the object at a second angle;
    a first retro-reflection unit for reflecting a first single reflected signal toward the first position on the object, wherein the first single reflected signal is a portion of the first signal that reflects off of the object;
    a second retro-reflection unit for reflecting a second single reflected signal toward the first position on the object, wherein the second single reflected signal is a portion of the second signal that reflects off of the object;
    a polarizing beam combiner for combining the first and second double reflected signals and directing the combined beams to a position sensitive detector to receive both the first and second double reflected signals for generating an output in response to the first and second double reflected signals;
    a processor, that receives the output and generates a material independent signal representing at least one of a height of the first position and a slope of the first position, the material independent signal being independent of the type of material comprising the object.

2. The system of claim 1 further comprising a spinning device for rotating the object to change the first position.

3. The system of claim 1, wherein the object is one of a thin film disk and a substrate.

4. The system of claim 1, wherein the object is a silicon wafer.

5. The system of claim 1, wherein the object is an optical component.

6. The system of claim 1, wherein the first and second electromagnetic signal sources are lasers.

7. The system of claim 6 wherein the first and second electromagnetic signal sources are one laser.

8. The system of claim 1, wherein the material independent signal is generated without the laser and the position sensitive detectors contacting the object.

9. The system of claim 1, for measuring the height of the object at the first position wherein a slope is ninety degrees, the slope representing the change in height between the first position and an adjacent position on the object.

10. A system to produce a symmetric optical beam profile, comprising:
    a first electromagnetic signal source for transmitting a first signal toward a first position on an object at a first angle, wherein a portion of the first signal is reflected from the object to generate a first reflected signal;
    a first retro-reflection unit positioned to receive a portion of the first reflected signal and to generate a first retro-reflected signal, wherein the first retro-reflected signal is retro-reflected toward the first position on the object;
    wherein a portion of the first retro-reflected signal is reflected from the object to generate a first double-reflected signal;
    a first position sensitive detector to receive the first double-reflected signal and to generate a first output in response to the first double-reflected signal;
    a second electromagnetic signal source for transmitting a second signal toward the first position on the object at a second angle, wherein a portion of the second signal is reflected from the object to generate a second reflected signal; and
    a second retro-reflection unit positioned to receive a portion of the second reflected signal and to generate a second retro-reflected signal, wherein the second retro-reflected signal is retro-reflected toward the first position on the object.

11. The system of claim 10, wherein the first reflected signal has an optical intensity profile having a centroid that is displaced from a central position.

12. The system of claim 10, wherein the first double-reflected signal has an optical intensity profile having a centroid that is located proximate a central position.

13. The system of claim 10, wherein the second reflected signal has an optical intensity profile having a centroid that is displaced from a central position.

14. The system of claim 10, wherein a portion of the second reflected signal is reflected from the object to generate a second double-reflected signal.

15. The system of claim 14, wherein the second double-reflected signal has an optical intensity profile having a centroid that is located proximate a central position.

16. The system of claim 14, further comprising a second position sensitive detector to receive the second double-reflected signal and to generate a second output in response to the second double-reflected signal signal.

17. The system of claim 16, further comprising a processor that receives the first and second output and generates a material independent signal representing at least one of a height of the first position and a slope of the first position, the material independent signal being independent of the type of material comprising the object.

18. A method to produce a symmetric optical beam profile, comprising:
    transmitting a first electromagnetic signal toward a first position on an object at a first angle, wherein a portion of the first electromagnetic signal is reflected from the object to generate a first reflected signal;
    receiving a portion of the first reflected signal in a first retro-reflection unit; and
    generating a first retro-reflected signal, wherein the first retro-reflected signal is retro-reflected toward the first position on the object; wherein a portion of the first retro-reflected signal is reflected from the object to generate a first double-reflected signal receiving the first double-reflected signal in a first position sensitive detector; and generating a first output in response to the first double-reflected signal;

transmitting a second electromagnetic signal toward the first position on the object at a second angle, wherein a portion of the second electromagnetic signal is reflected from the object to generate a second reflected signal;

receiving a portion of the second reflected signal in a second retro-reflection unit; and generating a second retro-reflected signal, wherein the second retro-reflected signal is retro-reflected toward the first position on the object.

19. The method of claim 18, wherein the first reflected signal has an optical intensity profile having a centroid that is displaced from a central position.

20. The method of claim 18, wherein the first double-reflected signal has an optical intensity profile having a centroid that is located proximate a central position.

21. The method of claim 18, wherein the second reflected signal has an optical intensity profile having a centroid that is displaced from a central position.

22. The method of claim 18, wherein a portion of the second reflected signal is reflected from the object to generate a second double-reflected signal.

23. The method of claim 22, wherein the second double-reflected signal has an optical intensity profile having a centroid that is located proximate a central position.

24. The method of claim 22, further comprising:

receiving the second double-reflected signal in a second position sensitive detector; and generating a second output in response to the second double-reflected signal.

25. The method of claim 24, further comprising:

receiving the first and second output in a processor; and generating a material independent signal representing at least one of a height of the first position and a slope of the first position, the material independent signal being independent of the type of material comprising the object.

* * * * *